United States Patent
Swerdlow et al.

(10) Patent No.: US 6,438,418 B1
(45) Date of Patent: *Aug. 20, 2002

(54) METHOD AND APPARATUS FOR REDUCTION OF PAIN FROM ELECTRIC SHOCK THERAPIES

(75) Inventors: Charles D. Swerdlow, Los Angeles; Neal R. Swerdlow, La Jolla, both of CA (US); James E. Brewer, Lino Lakes, MN (US)

(73) Assignee: Imperception, Incorporated, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/568,237

(22) Filed: May 5, 2000

Related U.S. Application Data

(63) Continuation of application No. 09/152,382, filed on Sep. 14, 1998, now Pat. No. 6,091,989.
(60) Provisional application No. 60/081,164, filed on Apr. 8, 1998.

(51) Int. Cl.[7] .............................................. A61N 1/362
(52) U.S. Cl. ............................................. 607/5; 607/63
(58) Field of Search ........................................... 607/63

(56) References Cited

U.S. PATENT DOCUMENTS

| | | | |
|---|---|---|---|
| 3,738,370 A | 6/1973 | Charms | 128/419 D |
| 4,316,472 A | 2/1982 | Mirowski et al. | 128/419 D |
| 4,375,817 A | 3/1983 | Engle et al. | 128/419 D |
| 4,384,585 A | 5/1983 | Zipes | 128/419 D |
| 4,577,633 A | 3/1986 | Berkovits et al. | 128/419 PG |
| 4,587,970 A | 5/1986 | Holley et al. | 128/419 PG |
| 4,726,380 A | 2/1988 | Vollmann et al. | 128/419 PG |
| 4,727,877 A | 3/1988 | Kallok | 128/419 D |
| 4,800,883 A | 1/1989 | Winstrom | 128/419 D |
| 4,809,697 A | 3/1989 | Causey, III et al. | 128/419 PT |
| 4,830,006 A | 5/1989 | Haluska et al. | 128/419 PG |
| 4,880,005 A | 11/1989 | Pless et al. | 128/419 PG |
| 4,949,719 A | 8/1990 | Pless et al. | 128/419 D |
| 4,953,551 A | 9/1990 | Mehra et al. | 128/419 D |
| 4,958,632 A | 9/1990 | Duggan | 128/419 PG |
| 5,117,824 A | 6/1992 | Keimel et al. | 128/419 D |
| 5,163,427 A | 11/1992 | Keimel | 128/419 D |
| 5,188,105 A | 2/1993 | Keimel | 128/419 D |
| 5,205,283 A | 4/1993 | Olson | 128/419 PG |
| 5,251,626 A | 10/1993 | Nickolls et al. | 607/14 |
| 5,269,298 A | 12/1993 | Adams et al. | 128/419 D |
| 5,282,837 A | 2/1994 | Adams et al. | 607/5 |
| 5,314,448 A | 5/1994 | Kroll et al. | 607/5 |
| 5,332,400 A | 7/1994 | Alferness | 607/5 |
| 5,366,485 A | 11/1994 | Kroll et al. | 607/5 |
| 5,425,749 A | 6/1995 | Adams | 607/5 |
| 5,439,481 A | 8/1995 | Adams | 607/5 |
| 5,545,186 A | 8/1996 | Olson et al. | 607/14 |
| 5,549,642 A | 8/1996 | Min et al. | 607/5 |
| 5,630,834 A | 5/1997 | Bardy | 607/5 |

OTHER PUBLICATIONS

Arzbaecher, Thomas et al., "Automatic Tachycardia Recognition" *PACE*, vol. 7 May–Jun. 1984, Part II, pp. 541–547.

(List continued on next page.)

*Primary Examiner*—Scott M. Getzow
(74) *Attorney, Agent, or Firm*—Skinner and Associates

(57) ABSTRACT

A method and apparatus for pretreating a patient prior to a therapeutic painful stimulus, comprising the application of pain inhibiting stimuli to a patient prior to an application of the therapeutic painful stimulus. Applying pain inhibiting stimuli comprises the steps of sensing a need for the therapeutic painful stimulus, preparing to deliver the pain inhibiting stimuli to the patient prior to applying the therapeutic painful stimulus, and delivering the pain inhibiting stimuli to the patient prior to applying the therapeutic painful stimulus. The method and apparatus are embodied in modern, fully automatic, fully implantable, single or dual chamber atrial or ventricular cardioverter-defibrillators. The pain inhibiting prepulse method is intended primarily for use in conscious patients but may also be used in sleeping patients.

23 Claims, 12 Drawing Sheets

OTHER PUBLICATIONS

Cohen, Michelle E., et al. "Sensory Magnitude Estimation in the Context of Reflex Modification", *Journal of Experimental Psychology*, 1981 vol. 7,No. 6, 1363–1370.

Cooper, Randolph A.S. MD, et al., "Internal Cardioversion of Atrial Fibrillation in Sheep" *Circulation*, vol. 87, No. 5, May 1993 pp. 1673–1686.

Cooper, Randolph A.S. MD, et al., "Internal Cardioversion of Atrial Fibrillation: Marked Reduction in Defibrillation Threwshold with Dual Current Pathways" *Circulation*, vol. 96, No.8 Oct. 21, 1997 pp 2693–2700.

Dunbar, Sandra B, et al. "Cognitive Therapy for Ventricular Dysrhythmia Patients" *Journal of Cardiovascular Nursing*, 1997; 12(1):33–44.

Hou, Charles Jia–Yin et al. MD, "Determination of Ventricular Vulnerable Period and Ventricular Fibrillation Threshold by Use of T–Wave Shocks in Patients Undergoing Implantation of Cardioverter/Defibrillators" *Circulation*, vol. 92, No. 9, Nov. 1, 1995, pp 2558–2564.

Johnson, Eric E. et al., "Monophasic and Biphasic Waveforms for Low Energy Internal Cardioversion of Atrial Fibrillation in Humans" *Circulation*, 1993, I592, #3184.

Lau, Chu–Pak, et al, "Initial Clinical Experience with an Implantable Human Atrial Defibrillator" *PACE*, vol. 20, Jan. 1997, Part II pp. 220–225.

Luderitz MD, Berndt, et al., "Patient Acceptance of Implantable Cardioverter Defibrillator Devices: Changing Attitudes" *American Heart Journal*, Apr. 1994 vol. 127, No. 4, Part 2, pp. 1179–1184.

Morris, Philip L., et al., "Psychiatric Morbidity Following Implantation of the Automatic Implantable Cardioverter Defibrillator" *Psychosomatics*, vol. 32 No. 1 Winter 1991, pp 58–64.

Moss, MD, Arthur J. et al., "Improved Survival with an Implanted Defibrillator in Patients with Coronary Disease at High Risk for Ventricular Arrhythmia" *The New England Journal of Medicine*, vol. 335, No. 26, Dec. 26, 1996 pp 1933–1940.

Mouchawar, G.A. et al., "Sural Nerve Sensory Thresholds of Defibrillation Waveforms" *JACC*, Feb. 1998, p. 373A, 886–5.

Murgatroyd MRCP, Francis D., et al., "Efficacy and Tolerability of Transvenous Low Energy Carioversion of Paroxysmal Atrial Fibrillation in Humans" *JACC*, vol. 25, No. 6 May 1995:1347–53.

Nathan, Anthony W., "Internal Transvenous Low Energy Cardioversion for the Treatment of Cardiac Arrhythmias" *British Heart Journal*,1984:52: 377–84.

Olson, Walter H., et al., "Onset and Stability for Ventricular Tachyarrhythmia Detection in an Implantable Pacer–Cardioverter–Defibrillator" *Computers in Cardiology*, Oct. 7–10, 1966, Boston MA IEEE Computer Society Press, pp. 167–170.

Perelman, M.S., et al., "Assessment of a Prototype Implantable Cardioverter for Ventricular Tachycardia" *British Heart Journal*, 1984; 52: 385–91.

Perlstein, William M., "Lead Stimulation Effects on Reflex Blink, Exogenous Brain Potentials, and Loudness Judgments" *Psychophysiology*, 30 (1993), 347–358.

Steinhaus MD, David M., et al. "Atrial Defibrillation: Are Low Energy Shocks Acceptable to Patients?" *PACE: NASPE Abstracts*, vol. 19, Apr. 1996, Part II, p. 625, #238.

Swerdlow MD, Neal R. et al., "Assessing the Validity of an Animal Model of Deficient Sensorimotor Gating in Schizophrenic Patients" *Archives of General Psychiatry*, Feb. 1994, vol. 51, pp139–154.

Swerdlow, Neal R, et al, "Neurophysiology and Neuropharmacology of Short Lead Interval Startle Modification" *StartleModificiation: Implications for Neuroscience, Cognitive Science, and Clinical Science*, Copyright 1999, Cambridge University Press, Chapter Six.

Thakor, Nitish V., et al, "Ventricular Tachycardia and Fibrillation Detection by a Sequential Hypothesis Testing Algorighm" *IEEE Transactions on Biomedical Engineering*, vol. 37, No. 9, Sep. 1990 pp 837–43.

Timmermans, C., et al. "Early Clinical Experience with the Metrix Automatic Implantable Atrial Defibrillator" *European Heart Journal*, 1997, p134, #892.

Zipes MD, Douglas P. et al., "Clinical Transvenous Cardioversion of Recurrent Life–Threatening Ventricular Tachyarrhythmias: Low Energy Synchronized Cardioversion of Ventricular Tachycardia and Termination of Ventricular Fibrillation in Patients Using a Catheter Electrode" *American Heart Journal*May 1982, vol. 103, No. 5, pp 789–794.

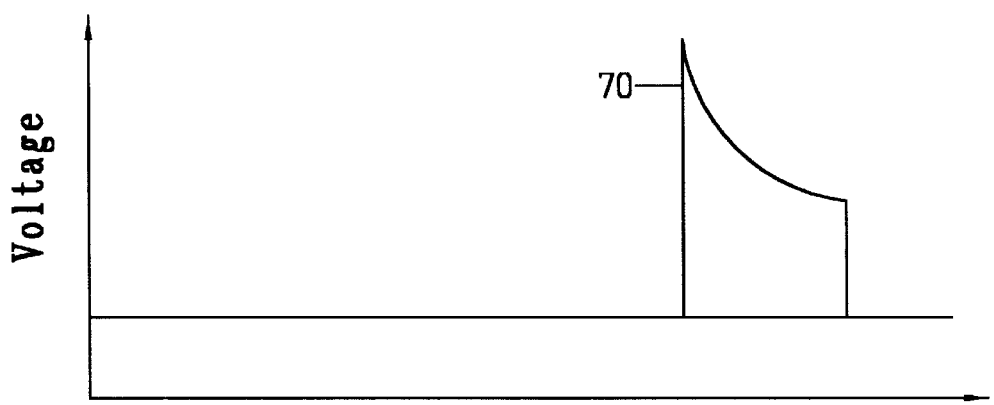
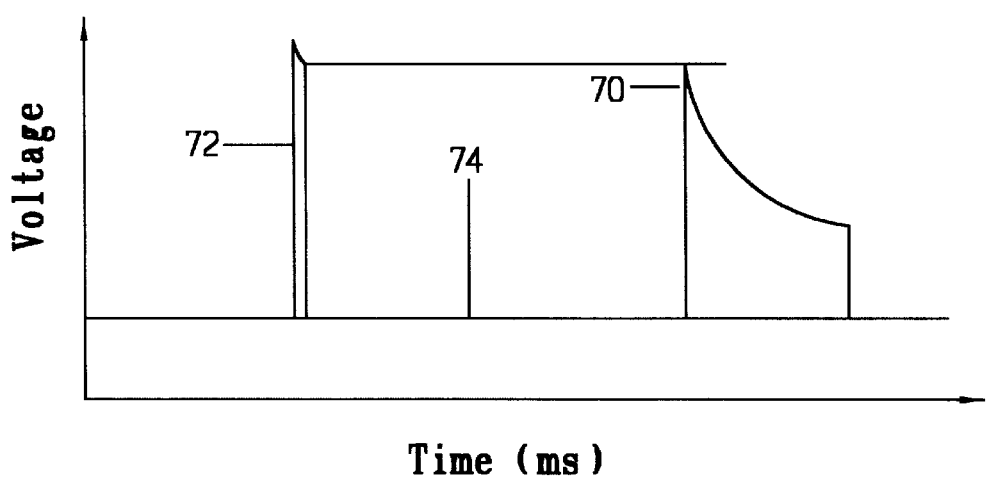
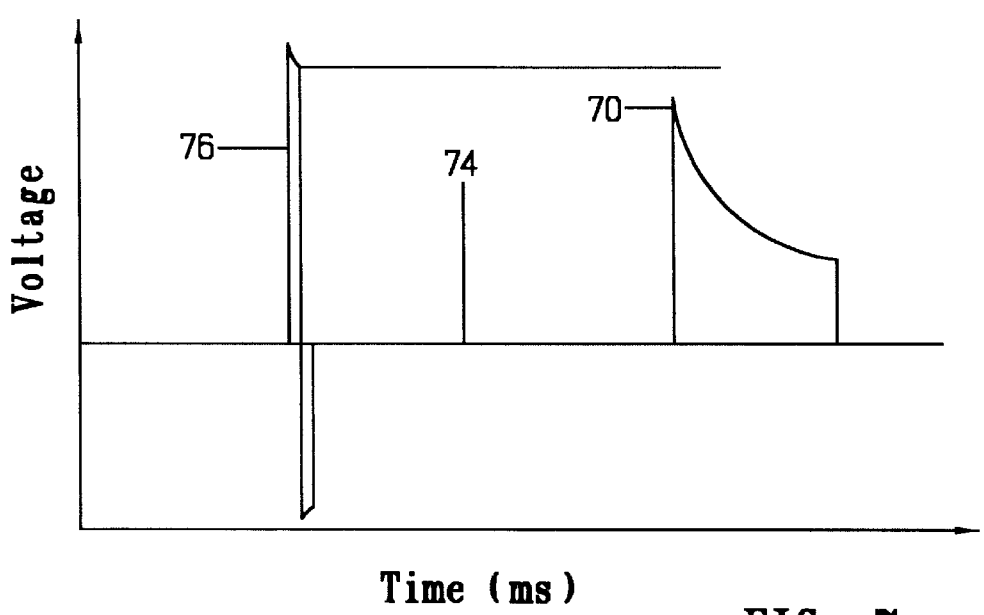
FIG. 7

METHOD AND APPARATUS FOR REDUCTION OF PAIN FROM ELECTRIC SHOCK THERAPIES

CROSS REFERENCE TO RELATED APPLICATIONS, IF ANY

This application is a continuation of application Ser. No. 09/152,382, filed Sep. 14, 1998, now U.S. Pat. No. 6,091,989.

This application claims the benefit under 35 U.S.C. §119 (e) of co-pending provisional application Serial No. 60/081,164, filed Apr. 8, 1998, which is hereby incorporated by reference.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

1. Field of the Invention.

This invention relates generally to therapeutic painful stimuli such as electric shock pulses, and more particularly to the process of reducing the pain associated with these therapeutic painful stimuli by modifying a patient's pain perception and response using prepulse inhibition (PPI). Further, this invention relates to therapeutic electric shocks delivered to patients by implantable cardioverter-defibrillators (ICDs) as treatment for atrial or ventricular arrhythmias. It relates particularly to reducing the pain associated with atrial defibrillation in a conscious patient.

2. Background Information.

Implantable cardioverter-defibrillators (ICDs) deliver high-voltage electrical pulses (shocks) to terminate cardiac arrhythmias. This treatment is highly successful, but it is severely painful and may even stun a patient temporarily. Initially, painful and startling therapeutic shocks were considered acceptable only as a treatment of last resort. Because of this, ICD therapy was restricted to ventricular arrhythmias which were both life-threatening and refractory to all other therapies. Subsequently, however, ICDs have become first-line therapy for patients with a history of life-threatening ventricular arrhythmias and patients at risk for life-threatening ventricular arrhythmias. Controlled studies have shown that ICDs are superior to alternative therapy for specific groups of these patients. These studies are the Multicenter Automatic Defibrillator Implantation Trial (Moss et al, N Engl J Med 1996; 335: 1933–1940) and the Antiarrythmics Versus Implantable Defibrillators Trial (Zipes et al, N Engl J Med 1997; 337: 1576–1583).

As ICD therapy has been applied to larger numbers of patients with ventricular arrhythmias, more attention has been paid to the painful and startling nature of the therapeutic shocks and the psychological complications of this therapy. These factors limit patient acceptance of ICD treatment of arrhythmias in conscious patients. A significant fraction of patients report anxiety and fear of painful ICD shocks ((1) Dougherty, Psychological reactions and family adjustment in shock versus no shock groups after implantation of internal cardioverter defibrillator, Heart Lung 1995; 24: 281–291—(2) Dunbar et al, Cognitive therapy for ventricular dysrhythmia patients, J Cardiovasc Nursing 1997; 12: 33–44—(3) Luderitz et al, Patient acceptance of ICD devices: Changing attitudes, Am Heart J 1994; 127: 1179–1184—(4) Morris et al, Psychiatric morbidity following implantation of the automatic ICD, Psychosomatics 1991; 32: 58–64). Shocks correlate with anxiety, psychiatric morbidity and psychological distress in ICD recipients. In one study 87.5% of patients experienced "nervousness" after a shock and 12.5% experienced "terror" or "fear." Patients who have experienced large numbers of repetitive shocks frequently suffer from a form of post-traumatic stress disorder.

Recently, ICD therapy has been applied to treatment of atrial arrhythmias, particularly atrial fibrillation ((1) Lau et al, Initial clinical experience with an implantable human atrial defibrillator, PACE 1997; 20: 220–225—(2) Timmersman et al, Early clinical experience with the Metrix automatic implantable atrial defibrillator, European Heart J 1997; 134). Although atrial fibrillation usually is not life-threatening, it is the most common arrhythmia requiring hospitalization in the United States. It causes potentially disabling symptoms of palpitations, shortness of breath, or chest pain and is an important cause of stroke.

The painful and startling nature of ICD shocks are considered a particular limitation for patient acceptance of ICD treatment of atrial fibrillation. It has been stated in recent published literature (Cooper et al, Internal atrial defibrillation in humans: Improved efficacy of biphasic waveforms and the importance of phase duration, Circulation 1997; 96: 2693–2700) that the ultimate acceptance of a fully automatic atrial defibrillator will depend on the reduction of pain to acceptable levels.

To this end, present state-of-the-art holds that a primary method of reducing the pain associated with these shocks is to reduce the strength of the shock pulse as measured by energy or voltage. This method requires a significant decrease in the shock strength required to defibrillate with a success rate of 50%. This shock strength is known as the defibrillation threshold. Recent studies have focused on reducing the atrial defibrillation threshold by altering the shape (waveform) of the delivered shock pulse or the locations of the electrodes (electrode configuration) through which these shocks are applied. The fundamental hypothesis is that lowering of the defibrillation threshold will permit atrial defibrillation with weaker shocks and thereby decrease the pain associated with these shocks in patients.

The shock strength judged tolerable for defibrillation in conscious patients has differed in previous studies, but is generally in the range of 0.1–0.5 joules (J). Zipes (Zipes et al, Clinical transvenous cardioversion of recurrent life-threatening ventricular tachyarrhythmias: Low energy synchronized cardioversion of ventricular tachycardia and termination of ventricular fibrillation in patients using a catheter electrode, Am Heart J 1982; 103: 789–794) reported that shocks of 0.5 J or less delivered between electrodes in the superior vena cava and right ventricle were tolerable for treatment of ventricular tachycardia. However, using the same electrode system, Perelman (Perelman et al, Assessment of prototype implantable cardioverter for ventricular tachycardia, Br Heart J 1984; 52: 385–391) found that 3 of 9 patients reported severe discomfort at a shock strength of 0.1 J. Nathan (Nathan et al, Internal transvenous low energy cardioversion for the treatment of cardiac arrhythmias, Br Heart J 1984; 52: 377) delivered transvenous shocks to 19 conscious patients for various atrial and ventricular arrhythmias. Fourteen of 19 patients described severe discomfort with shock strengths 0.5 J. Murgatroyd (Murgatroyd et al, Efficacy and tolerability of transvenous low energy cardioversion of paroxysmal atrial fibrillation in humans, J Am Coll Cardiol 1995; 25: 1347–1353) determined the range of tolerable shock strengths for the most favorable electrode configuration for atrial defibrillation (right atrium to distal coronary sinus). Although the range of shock strengths tolerated without severe discomfort was 0.1 to 1.2 J, seven of 19 patients found even 0.1 J shocks intolerable. Using a different electrode system, Steinhaus (Steinhaus et al, Atrial defibrillation: are low energy shocks acceptable to patients? PACE 1996; 19: 625) delivered shocks of 0.4 J and 2.0 J shocks in randomized order. Patients reported no difference in perceived pain between the two shock strengths. Both shock strengths were given discomfort scores of approximately 7 on a scale of 0–10.

However, Steinhaus found that the second shock was judged significantly more painful than the first shock, independent of shock strength. This observation is important because a strategy for reducing pain in defibrillation of arrhythmias which are not life-threatening (such as atrial fibrillation) contemplates clinical use of defibrillation shocks with strength near the defibrillation threshold. The hypothesis is that, even if multiple shocks are required to terminate the arrhythmia, multiple weaker shocks will be better tolerated than one strong shock. Steinhaus' data suggest that any clinical benefit in pain reduction achieved by delivering clinical defibrillation shocks with strength near the defibrillation threshold is likely to be offset by the increased discomfort associated with subsequent shocks as weak as 0.4 J.

Data reported for atrial defibrillation thresholds must be considered in the perspective of these reported values for tolerable shock strengths. Cooper (Cooper et al, Internal cardioversion of atrial fibrillation in sheep, Circulation 1993; 87: 1673–1686) measured the atrial defibrillation threshold for multiple waveforms and electrode configurations in sheep. They showed that a specific biphasic waveform (3 ms phase 1 and 3 ms phase 2) and a specific electrode configuration (right atrial appendage to distal coronary sinus) resulted in the lowest atrial defibrillation threshold for the combinations of electrode configurations and waveforms tested (1.3±0.4 J). However, use of this waveform and electrode configuration in humans with paroxysmal (intermittent) atrial fibrillation, the principal treatment population for atrial ICDs, resulted in atrial defibrillation thresholds approximately twice as high as in sheep. Johnson (Johnson et al, Circulation 1993; I 592) reported a value of 2.5±1.4 J and Murgatroyd (Murgatroyd et al, J Am Coll Cardiol 1995; 25: 1347–1353) reported a value of 2.2±1.0 J. Therefore, the prior art does not teach a method sufficient for the reduction of a patient's perceived pain during atrial defibrillation shocks.

More recently, Cooper (Cooper et al, Internal cardioversion of atrial fibrillation: Marked reduction in defibrillation threshold with dual current pathways, Circulation 1997; 96: 2693–2700) showed that sequential shocks delivered through two different sets of electrodes significantly decreased atrial defibrillation thresholds in sheep. The defibrillation threshold for this complex method (0.36±0.13 J) was significantly lower than that of the best single-pathway method (1.3±0.3 J). Since the average atrial defibrillation thresholds in sheep are approximately half that of the average atrial defibrillation thresholds for patients with paroxysmal atrial fibrillation, it was estimated that this newly determined method would provide average atrial defibrillation thresholds of slightly less than 1 J in patients. Thus, despite the additional complexity of the implant procedure and possible additional short and long-term morbidity associated with this new method, it is not likely to permit atrial defibrillation shocks without severe discomfort in the majority of patients. Therefore, this prior art does not teach a method sufficient for the significant reduction of a patient's perceived pain during atrial defibrillation. This prior art moreover requires the increased cost, surgical complexity, and risk associated with two additional electrodes.

The method and apparatus of U.S. Pat. No. 5,332,400 issued to Alferness discloses an implantable atrial defibrillator that provides a warning to a patient prior to delivery of an atrial shock pulse to cardiovert or defibrillate the patient's atrial arrhythmia. The atrial defibrillator applies a warning electrical shock to the patient's atria when the apparatus determines that the atria require cardioversion or defibrillation. The warning shock has an energy level lower than that required to treat the arrhythmia but high enough to be discerned by the patient without pain or other discomfort. The purpose of this warning is to provide sufficient time in advance of the therapeutic shock (in the range of 1 to 20 minutes) to afford a patient the opportunity to prepare for this painful and startling therapy. The Alferness method and apparatus demonstrate the limitation of the prior art to significantly reduce the extreme pain perceived by a patient when the defibrillation therapy is applied.

The method and apparatus of U.S. Pat. No. 5,439,481 issued to Adams discloses an implantable atrial and ventricular defibrillator that diagnoses atrial and ventricular arrhythmias, automatically treats the ventricular arrhythmias, but allows discretionary treatment of the atrial arrhythmias. Such discretionary control permits the patient to forego painful atrial defibrillation shocks based on a medical assessment that the atrial arrhythmia is not significantly dysfunctional and is amenable to less immediate and less urgent medical treatment. The Adams method and apparatus further demonstrate the limitation of the prior art to alleviate the extreme pain perceived by a patient when atrial defibrillation therapy is applied.

The method and apparatus of U.S. Pat. No. 5,630,834 issued to Bardy discloses an implantable atrial defibrillator that determines whether a patient is asleep prior to delivery of an atrial shock pulse. Defibrillation shocks that would be extremely painful to a conscious patient are delivered only when a patient is asleep. Bardy states that although numerous patents and applications attempt to optimize shock waveforms and electrode systems to reduce defibrillation thresholds (and therefore pain), the reliable accomplishment of low thresholds for all patients will remain a difficult and perhaps infeasible objective. This method may require a patient to remain in atrial fibrillation for many hours until the patient falls asleep. Thus it is not practical for some patients who become symptomatic shortly after the onset of atrial fibrillation or for patients with ventricular arrhythmias who typically require treatment as soon as possible after the onset of the arrhythmia. Further, some patients have reported being awakened from sleep by painful and startling ICD shocks. Thus, administration of shocks during sleep is painful in some patients. In addition, a patient's knowledge that he/she may be shocked while asleep may result in anticipatory anxiety that interferes with sleep. The Bardy method and apparatus further demonstrate the limitation of the prior art to significantly reduce the extreme pain perceived by a conscious patient when defibrillation therapy is applied.

We therefore describe a method and apparatus to significantly diminish or eliminate the perceived pain by reducing the perceived intensity of defibrillation shocks and by inhibiting the startle response associated with these shocks. The clinical basis for the present invention is the fundamental physiologic principal of PPI. As will be appreciated from a review of the background discussion and the detailed description of the preferred embodiments, the present invention overcomes the limitations and shortcomings of the prior art.

In the field of neurophysiologic and neuropsychiatric research, it has been long appreciated that the experienced intensity of a strong, abrupt stimulus, and the behavioral (startle) response to this stimulus can be diminished by delivering a weak stimulus 30–500 ms prior to the strong stimulus ((1) Cohen et al, Sensory magnitude estimation in the context of reflex modification, J Exper Psychology 1981; 7: 1363–1370—(2) Swerdlow et al, "Neurophysiology and neuropharmacology of short lead interval startle modification," Chapter 6 of *Startle Modification: Implications for Neuroscience, Cognitive Science, and Clinical Science*, Dawson et al, Cambridge Univ Press, 1997). This physiologic suppression of the startle reflex is referred to as prepulse inhibition (PPI). PPI decreases both the motor (startle) response and the subject's perception of the intensity of the startling stimulus (pain). Normal human subjects consistently rate startling stimuli as significantly less intense if these stimuli are preceded by an appropriate weak prestimulus than if they were presented alone.

The neural circuitry responsible for the sensorimotor modulation of PPI has been studied extensively. These studies indicate that PPI reflects the activation of ubiquitous, "hard-wired," behavioral gating processes that are regulated by forebrain neural circuitry. PPI occurs in virtually all mammals, and can be elicited in humans and humans and experimental animals using near-identical stimuli to produce strikingly similar response patterns (Swerdlow et al, Assessing the validity of an animal model of deficient sensorimotor gating in schizophrenic patients, Arch Gen Psychiatry 1994; 51: 139–154). The importance of these findings is that optimal stimulus parameters for PPI, and the neural substrates that regulate PPI, can be studied easily in animal models. This capability facilitates the application of PPI principles as disclosed in the preferred embodiments of the present invention.

In one preferred embodiment of the present invention, a single, low-voltage, short-duration pulse (the prepulse) precedes a high-voltage shock pulse. The time interval between the prepulse and the shock pulse is set between 30 to 500 ms. The specific time interval is determined by a testing method which identifies the optimal interval for PPI. The prepulse and therapeutic shocks may have arbitrary waveforms which are not necessarily identical. For example, these may include monophasic or biphasic capacitive-discharge pulses of the type presently used in ICDs, or a pulse waveform constructed specifically to reduce pain, such as a rounded, slow-rise time, or ascending ramp waveform (Mouchawar et al, Sural nerve sensory thresholds of defibrillation waveforms, J Amer Coll Card 1998: 31 (Suppl A): 373). At the time of implant of an atrial, ventricular, or dual-chamber ICD with the present invention incorporated therein, a physician first determines an appropriate electrode system for a given patient and the appropriate cardioversion or defibrillation energy setting for that patient and electrode system. The physician then adjusts the amplitude of the prepulse and intervening time interval between the prepulse and the therapeutic shock pulse so as to significantly reduce or eliminate the patient's perceived pain and startle response caused by the shock pulse. Typically, the shock strength required for cardioversion or defibrillation is determined while the patient is under the influence of a short-acting anesthetic. The prepulse amplitude and time interval are adjusted in the conscious patient after the effects of any short-acting anesthetic has dissipated. Alternatively, the prepulse amplitude and time interval are adjusted at a postoperative programming study.

It is important to note that defibrillation shocks are associated with a prominent startle responses in many patients. Studies of other types of startle responses demonstrate that startle responses are actually increased when warning stimuli preceded the startling stimuli at intervals (>1 sec) that are adequate to evoke conscious anticipation of the startling stimulus (prepulse facilitation). Thus a "warning" prestimulus which is sufficiently early to evoke a conscious response prior to an ICD shock is likely to increase the shock-induced startle effect. ICD recipients report severe discomfort related specifically to the startling effects of defibrillating shocks. A long-delay "warning" prestimulus is a programmable option in some ICDs. This feature is rarely activated because patients experience anxiety during the anticipatory interval following the "warning" prestimulus. The present invention overcomes these problems by suppressing the painful "jolt" associated with the defibrillation-induced startle reflex, using automatic, preconscious mechanisms evoked during a time interval (30–500 ms) which is too short to stimulate anticipatory anxiety.

The methods and devices of the prior art that most nearly approach the novel features of the present invention, which uses PPI to reduce the perceived pain of therapeutic electrical stimuli delivered to a conscious patient, are, in fact, quite remote from it. Their marginal relevance can best be appreciated by a short, comparative description.

The method and apparatus of U.S. Pat. Nos. 5,314,448 and 5,366,485 issued to Kroll and Adams disclose electrical pretreatment to a ventricular fibrillating heart to permit the applied shock pulse to defibrillate the ventricles with less energy than may otherwise be required. Pretreatment pulses and the treatment shock are delivered through the same electrodes. The underlying hypothesis asserts that electrical pretreatment of a fibrillating heart is expected to achieve temporal organization of the ventricular cardiac cells, thereby diminishing the demands imposed on the defibrillation threshold for the defibrillating shock pulse. As will become apparent in the description of the preferred embodiments, the present invention differs significantly from this prior art. The concept of electrical pretreatment of a fibrillating heart to assist the defibrillating shock pulse by reducing its level of required energy through temporal cardiac organization is completely absent from the present invention.

The method and apparatus of U.S. Pat. No. 5,425,749 issued to Adams discloses the delivery of an electrical preemptive cardioversion shock to a patient determined to have a life-threatening arrhythmia such as ventricular fibrillation. The underlying hypothesis asserts that the shock strength required for defibrillation is directly related to the duration of fibrillation and that an electrical preemptive shock delivered as soon as possible following the onset of an arrhythmia will reduce the total energy requirements for cardioversion or defibrillation. The preemptive shock is thus delivered several seconds before the main cardioverting or defibrillating pulse. As will become apparent in the description of the preferred embodiments, the present invention differs significantly from this prior art. The concept of electrical preemptive cardioversion or defibrillation to quickly treat a patient and thereby to significantly reduce the size and energy requirements of a defibrillator is completely absent from the present invention.

Despite the need in the art for an ICD apparatus or methods which overcome the shortcomings and limitations of the prior art, none insofar as is known has been developed or proposed. Accordingly, it is an object of the present invention to provide an implantable atrial, ventricular, or dual-chamber ICD method and apparatus that applies the clinical science related to sensorimotor gating to reduce or eliminate the perceived intensity of, and startle response to, the ICD's shock pulse. The present invention reduces or eliminates the pain by delivering a timed prepulse that reduces the perceived intensity of the shock pulse, and inhibits the startle response to the shock pulse. There are no such teachings in the prior art.

BRIEF SUMMARY OF THE INVENTION

The present invention provides a method and apparatus to pretreat a patient prior to a therapeutic painful stimulus, comprising the step of applying at least one pain inhibiting stimulus to a first part of a patient's body prior to an application of the therapeutic painful stimulus to the same part or a second part of a patient's body. This method is intended primarily for use in conscious patients, but it may also be used in sleeping patients.

The benefits of this invention will become clear and will be best appreciated with reference to the detailed description of the preferred embodiments. Other objects, advantages and novel features will be apparent from the description when read in conjunction with the appended claims and attached drawings.

BRIEF DESCRIPTION OF THE SEVERAL VIEWS OF THE DRAWING

FIG. 7 illustrates first a monophasic atrial or ventricular defibrillation pulse, second a high amplitude, pain inhibiting, monophasic prepulse preceding the monophasic atrial or ventricular defibrillation pulse, and third a high amplitude, pain inhibiting, biphasic prepulse preceding the monophasic atrial or ventricular defibrillation pulse.

DETAILED DESCRIPTION

Clinical Background and Theory of Operation

Figure 1:
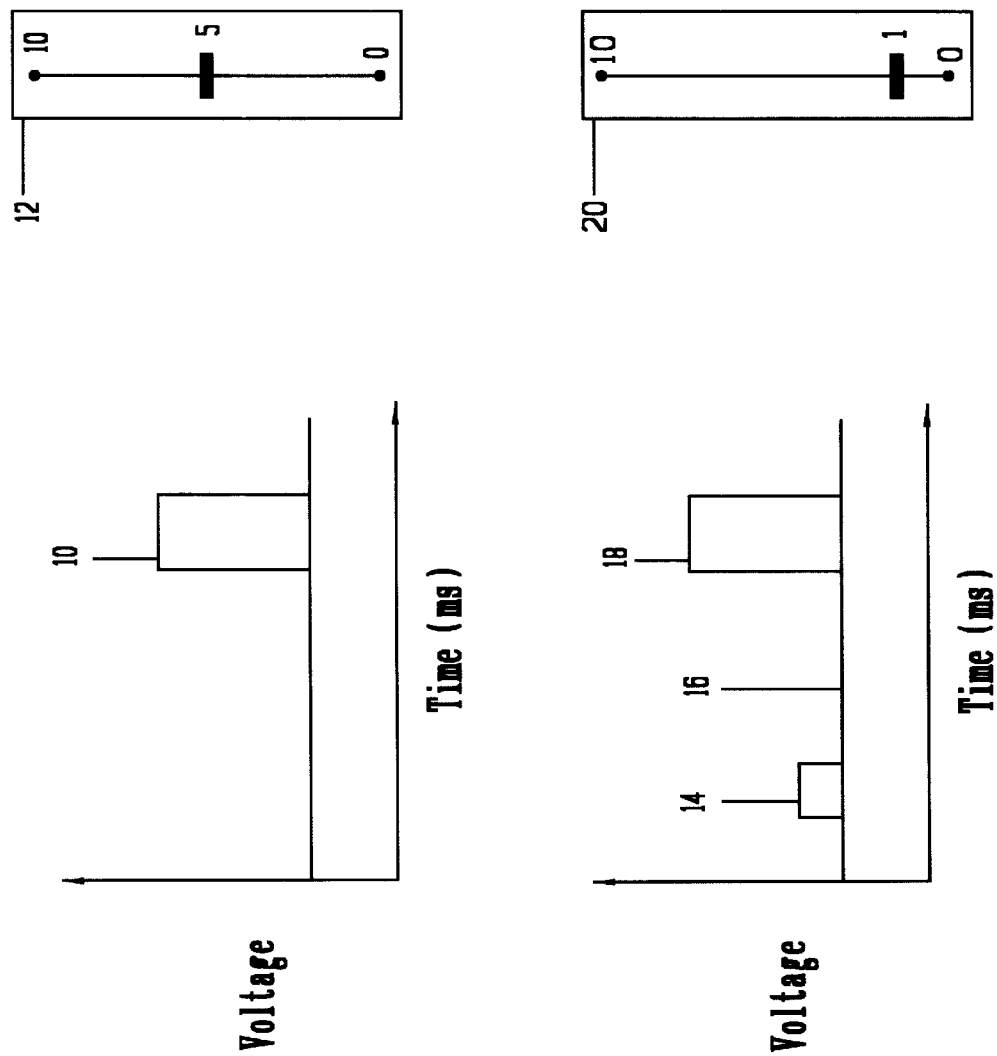
FIG. 1 illustrates a single, startling pulse, an associated measurement of perceived pain and startle reflex magnitude, a prepulse preceding the single, startling pulse by a 30–500 ms interval, and an associated, significant reduction of the perceived pain and startle response exhibited by a patient.

Startle response is a well-understood simple behavior that has been studied systematically in the field of neurobiology. The systematic study has drawn on the characteristics of startle as a quantifiable, parametrically sensitive behavior of animals and humans. The startle response is regulated by forebrain circuitry and appears to exhibit striking similarities across species. The startle response demonstrates important forms of plasticity, including habituation and fear-potentiation. One form of startle plasticity relates to its amplitude modulation when the startle reflex is preceded by a prestimulus, or prepulse. The amplitude modulation is called PPI, which is the normal suppression of the startle reflex when the intense startling stimulus is preceded 30 to 500 ms by a relatively weak prestimulus. In PPI, a weak prestimulus inhibits a reflex response to a powerful sensory stimulus. Virtually all mammals and primates exhibit PPI. PPI reflects the activation of ubiquitous, "hard-wired," sensorimotor gating processes that are regulated by forebrain neural circuitry.

Sensorimotor (startle response) modulation can also result in the potentiation of the startle reflex. Startle magnitude is increased when the startling stimulus is preceded at very short (<20 ms) or long intervals (>1000 ms) by prestimuli. This modulation is called prepulse facilitation, and is most evident with weak prestimuli. Prestimulus modulation changes from facilitation to inhibition with increasing prepulse interval and intensity. Prepulse facilitation reappears as the time intervals become extended. It is not known whether PPI and prepulse facilitation are opposing forms of sensorimotor modulation that result from activity within either a single brain system or two separable substrates.

The brain circuitry that mediates the inhibitory effect of the prestimulus does not deviate from the primary startle circuit by more than 1 to 2 neurons, with an approximate 7.5 ms conduction time "out" from and 7.5 ms conduction time "back" to the primary startle circuit. The circuitry that mediates PPI is simple and is integrally related to the primary startle circuit. The forebrain circuitry "sets the gain" for PPI, involving several different neurotransmitter systems that regulate the amount of sensorimotor inhibition. Therefore, the regulation of startle facilitation is maximal with weak prestimuli at very short time intervals and startle inhibition is maximal with more intense prestimuli at relatively "longer" short time intervals.

In addition to suppressing the motor component of the startle reflex response to intense, abrupt stimuli, prestimuli modify the perceived intensity of these stimuli. Subjects rate the intensity of loud noise bursts as being lower when those bursts are preceded by prepulses, compared to noise bursts without prepulses (Perlstein et al, Lead stimulation effects on reflex blink, exogenous brain potentials, and loudness judgments, Psychophysiology 1993; 30: 347–358). Thus, prepulses inhibit both the perceived intensity of, and the motoric response to, startling stimuli.

Figure 2:
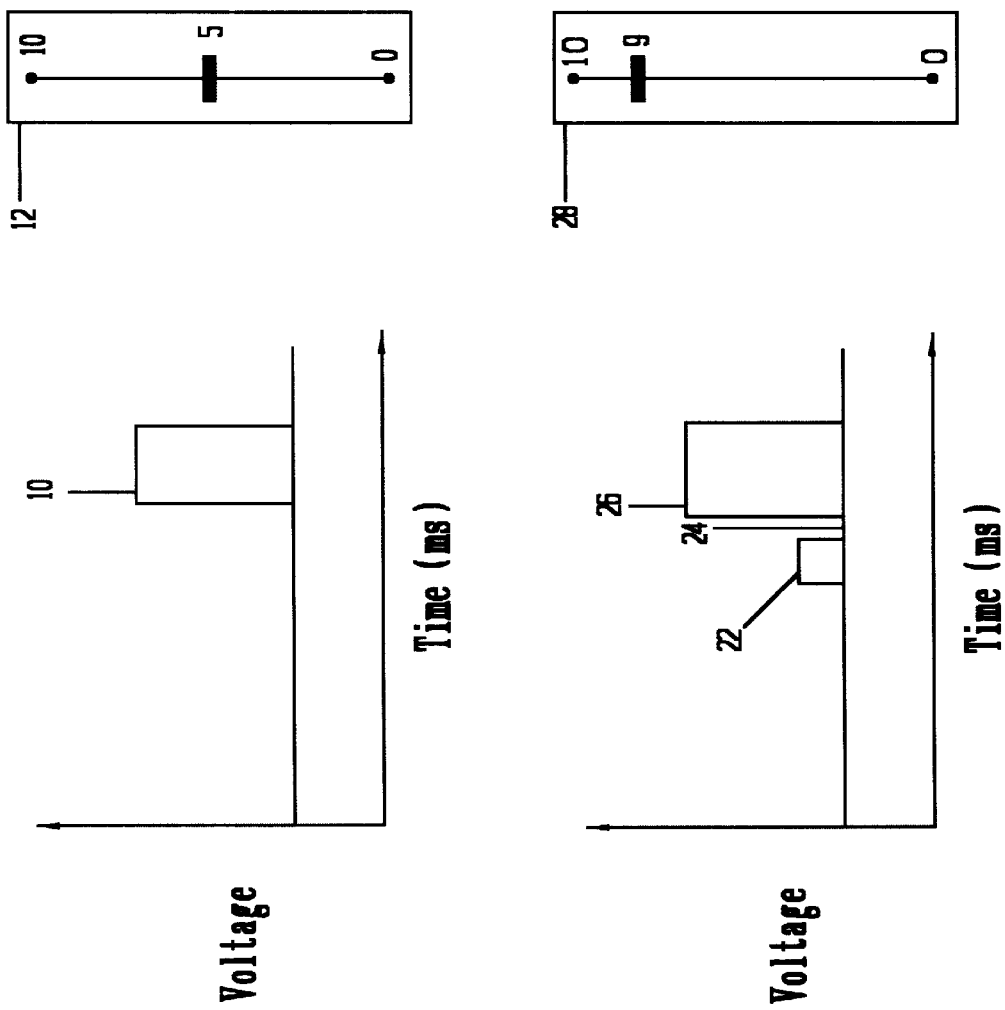
FIG. 2 illustrates a single, startling pulse, an associated measurement of perceived pain and startle reflex magnitude, a prepulse preceding the single, startling pulse by a 0.1–20 ms interval, and an associated, significant accentuation of the perceived pain and startle response exhibited by a patient.

Most important to the present invention, the cardioversion or defibrillation pulse delivered by an ICD result in subjective pain and discomfort perceived by a patient as well as an objective, physiologic, motoric, startle response by the patient. FIG. 1 and FIG. 2 illustrate the underlying neurobiologic principles in the attenuation or accentuation of pain through startle response modulation using an electrical prepulse.

FIG. 1 demonstrates the amplitude modulation of a patient's perception of or response to a painful stimulus due to PPI. The top time-versus-voltage graph in FIG. 1 represents an intense, painful stimulus 10 to a patient, such as a defibrillation shock pulse, and the patient's perception of or response to that stimulus illustrated in the bar graph 12. Note that in FIG. 1 and subsequent FIG. 2, bar graph 12 may represent a measure either of a patient's subjective perception of the painful stimulus 10 or physiologic response to the painful stimulus 10, such as startle. The measured value of the patient's perception of or response to painful stimulus 10 is illustrated in the bar graph 12 as a "5" on a scale from 0 to 10, with 10 representing a measurement of greatest intensity. The bottom time-versus-voltage graph in FIG. 1 represents an intense, painful stimulus 18 to a patient, such as a defibrillation shock pulse. Painful stimulus 18 is preceded by a weaker prepulse 14 and separated by a predetermined time interval 16. The patient's associated perception of or response to the combined effects of painful stimulus 18 and prepulse 14 are illustrated in the bar graph 20, which corresponds to the bar graph 12 in the top panel. The measured value is illustrated in the bar graph 20 as a "1" on a scale from 0 to 10. FIG. 1 thereby illustrates that the amplitude, duration, and preceding time interval for the prepulse were predetermined to modulate the patient's response in the form of PPI, thereby reducing a patient's pain, discomfort, or startle.

Similarly, FIG. 2 demonstrates the amplitude modulation of a patient's perception of or response to a painful stimulus due to prepulse facilitation. The top time-versus-voltage graph in FIG. 2 again represents an intense stimulus 10 to a patient, such as a defibrillation shock pulse, and the patient's subjective perception of or physiologic response to the painful stimulus 10, such as startle. The measured value of the patient's perception of or response to painful stimulus 10 is illustrated in the bar graph 12 as a "5" on a scale from 0 to 10, with 10 representing a measurement of greatest pain. The top graph in FIG. 2 is identical in all respects to the top graph in FIG. 1. The bottom time-versus-voltage graph in FIG. 2 represents an intense, painful stimulus 26 to a patient, such as a defibrillation shock pulse, which is preceded by a weaker prepulse 22. Prepulse 22 precedes intense stimulus 26 by predetermined time interval 24. Note that predetermined time interval 24 is much shorter than predetermined time interval 16 of FIG. 1. The patient's associated perception of or response to the combined effects of painful stimulus 26 and prepulse 22 are illustrated in the bar graph 23, which corresponds to the bar graph 12 in the top panel and bar graph 20 in the bottom panel of FIG. 1. This measured value is illustrated in the bar graph 28 as a "9" on a scale from 0 to 10. FIG. 2 thereby illustrates that the amplitude, duration, and preceding time interval for the prepulse were predetermined to modulate the patient's response in the form of prepulse facilitation, thereby accentuating a patient's pain, discomfort, or startle.

Although both the prepulse and startling pulse are shown in FIGS. 1 and 2 as square waves for illustrative purposes, the pulses may have arbitrary waveform shape and varying amplitude and duration.

Many studies have been conducted to characterize PPI in humans. In a typical method for demonstrating the increase in PPI with increased prepulse intensity (Swerdlow et al, Assessing the validity of an animal model of deficient sensorimotor gating in schizophrenic patients, Arch Gen Psychiatry 1994; 51: 139–154), acoustic stimuli are delivered through headphones with a continuous 70-dB(A) background white noise. Startle pulses (40 ms-duration bursts of 118-dB(A) white noise) is presented alone or 100 ms following a 20 ms-duration prepulse burst of white noise at 2, 4, 8, or 16 dB(A) above the background noise. Each startle pulse and prepulse combination is administered multiple times, in random order. PPI is defined as the percentage of reduction in startle amplitude in the presence of the prepulse compared with the amplitude in the absence of the prepulse. Thus, a high percentage score indicates a high degree of PPI. Analysis of variance (ANOVA) with repeated measures on trial type can be used to reveal a significant effect of prepulse intensity on PPI Additionally, a threshold sensitivity for the reduction of startle amplitude can be identified. Using the stimulus parameters described above, this typically occurs with prepulse intensities approximately 4 dB above the background noise.

Figure 3:
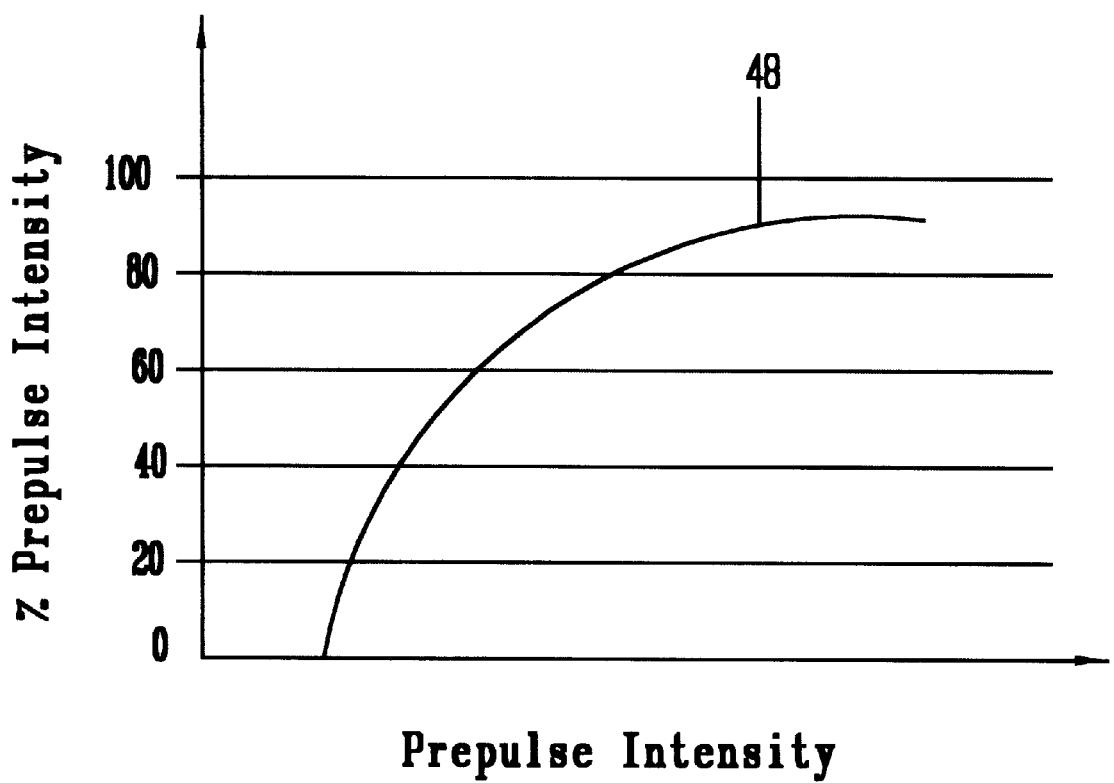
FIG. 3 illustrates an empirically determined relationship of prepulse intensity to the percentage of PPI.

FIG. 3 clearly illustrates the important relationship 48 between prepulse intensity and the percentage of PPI for a constant prepulse interval (time between prepulse and pulse). The reduction of startle amplitude increases with increasing prepulse intensity when prepulse interval is held constant. The results from the illustrative, acoustic trial have been repeated for other intense stimuli (e.g. air puff, shock and light flash) and their associated perceived pain or physiologic response. The results are consistent with the illustrated relationship and demonstrate a universal relationship of PPI to startle response across stimulus modalities. As importantly, it has been shown that PPI occurs when the prestimulus and the startling stimulus are in the same or different sensory modalities. One example would be an acoustically derived prestimulus coupled with a startling stimulus that is electrically derived. Another example would be a tactile derived prestimulus coupled with a startling stimulus that is optically derived.

Preclinical studies suggest that certain medications can increase the amount of prepulse inhibition. For example, in some conditions, prepulse inhibition was enhanced by the atypical antipsychotic clozapine. Because increased PPI may be associated with a reduction in the experience of, and response to a startling stimulus, it may be desirable, under certain circumstances, to utilize specific medications to enhance the effectiveness of PPI in reducing the perception of, and/or response to a defibrillation shock. Medication may be administered on an as-needed basis to patients in advance of a period of planned defibrillation, or on an ongoing basis to patients who require intermittent defibrillation.

Description of the Principle Physical Elements

Figure 4A:
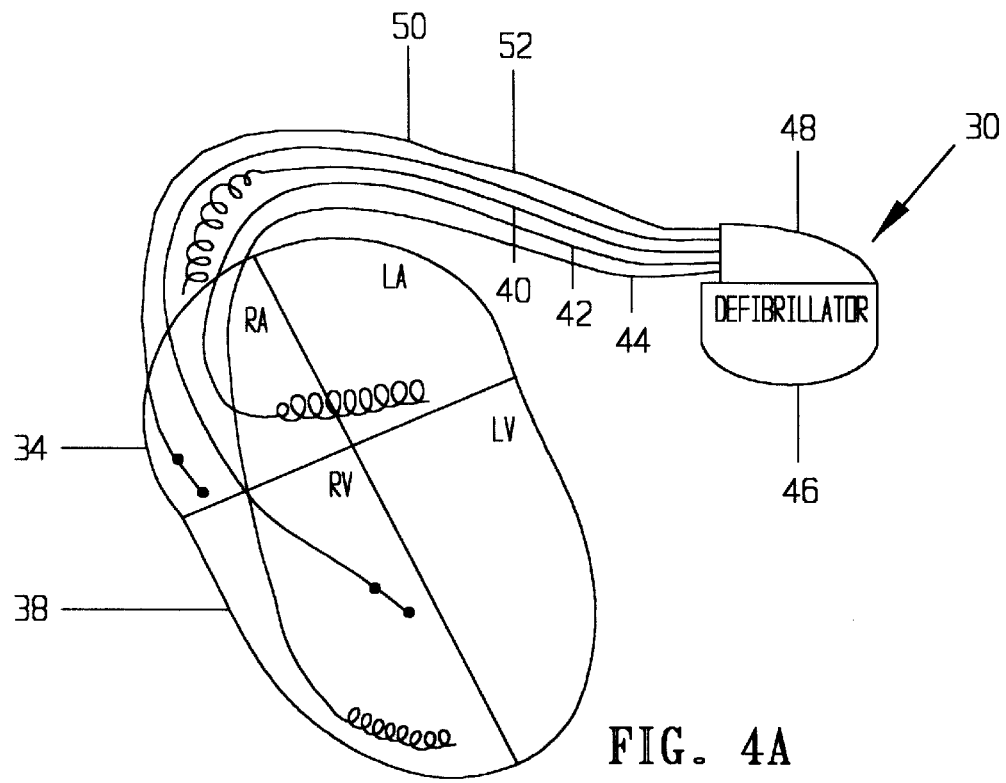
FIG. 4A illustrates an active housing ventricular ICD implanted pectorally and attached to transvenous electrodes placed into the superior vena cava, coronary sinus, and right ventricle of a patient's heart, and further attached to tip to ring pacing and sensing electrodes placed into the right ventricle of a patient's heart.
Figure 4B:
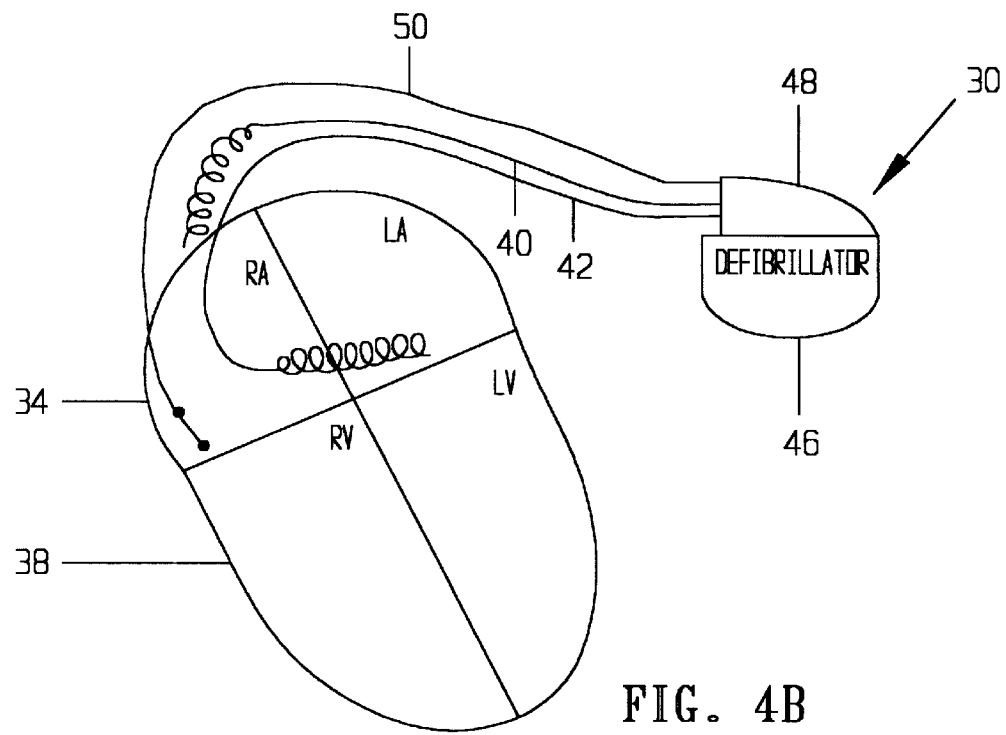
FIG. 4B illustrates an active housing atrial or dual chamber implanted pectorally and attached to transvenous electrodes placed into the superior vena cava, right ventricle and coronary sinus of a patient's heart, and further attached to bipolar pacing and sensing electrodes placed into the right atrium and right ventricle of a patient's heart.

FIGS. 4A, 4B, 5 and 6 illustrate the principle physical elements of the invention. The figures illustrate a fully implantable atrial or ventricular cardioverter—defibrillator pulse generator (ICD) 30 that embodies the present invention and shown in association with a schematically illustrated human heart 34 and 38. The portions of the heart illustrated in FIGS. 4A and 4B are the right atrium 34 (RA), the left atrium (LA), the right ventricle 38 (RV), and the left ventricle (LV).

ICD pulse generator 30 generally includes a housing 46 for hermetically sealing the internal circuits and programming 150 of ICD 30 to be described hereinafter, a right atrial/superior vena cava endocardial high-voltage lead 40, a coronary sinus/great cardiac vein, endocardial high-voltage lead 42, a right ventricle endocardial high-voltage lead 44, a right atrium pace/sense lead 50, and a right ventricle pace/sense lead 52. Each of the leads comprise an insulative lead body. The housing 46 of ICD 30 may be provided with some or all portions without plastic insulation (for example parylene or silicone rubber). The uninsulated portions of the housing 46 optionally serve as a prepulse or defibrillation electrode, used to deliver a prepulse or a high-voltage defibrillation shock pulse to the atria, ventricles or both atria and ventricles. High-voltage leads 40, 42, and 44 further comprise electrodes capable of conducting high voltage currents and defibrillation coil electrodes. They may be fabricated from platinum, platinum alloy, or other materials known to be usable in ICD electrodes. Leads 40, 42, and 44 are used to deliver a prepulse or a high-voltage defibrillation shock pulse to either the atria or ventricles. Lead 50 further comprise a tip electrode and a ring electrode, and is constructed to enable bipolar sensing of electrical activations of the right atrium 34. Lead 52 further comprise a tip electrode and a ring electrode, and is constructed to enable bipolar sensing of electrical activations of the right ventricle 38. Although they are shown separately in FIG. 4 for clarity, one or more of the high-voltage leads 40, 42, and 44 and one or more of the pace-sense leads 50 and 52 may be combined into a single multiconductor lead. The enclosure 46 and the endocardial leads 40, 42, 44, 50 and 52 are arranged for establishing electrical contact with the heart and to be implanted beneath the skin of a patient and so as to render ICD 30 fully implantable.

Within the enclosure 46, ICD 30 includes electrode switching circuitry 188. Leads 40, 42, 44, 50 and 52 are coupled to the electrode switching circuitry via connector block 48. Leads 50 and 52 are further coupled communicatively to pacer timing/control circuitry 174 and to electrogram sensing and conditioning circuitry 154. Lead 50 therefore forms a complete pace/sensing lead system for pacing and sensing electrical activations of the right atrium. Lead 52 therefore forms a complete pace/sensing lead system for pacing and sensing electrical activations of the right ventricle.

Figure 5:
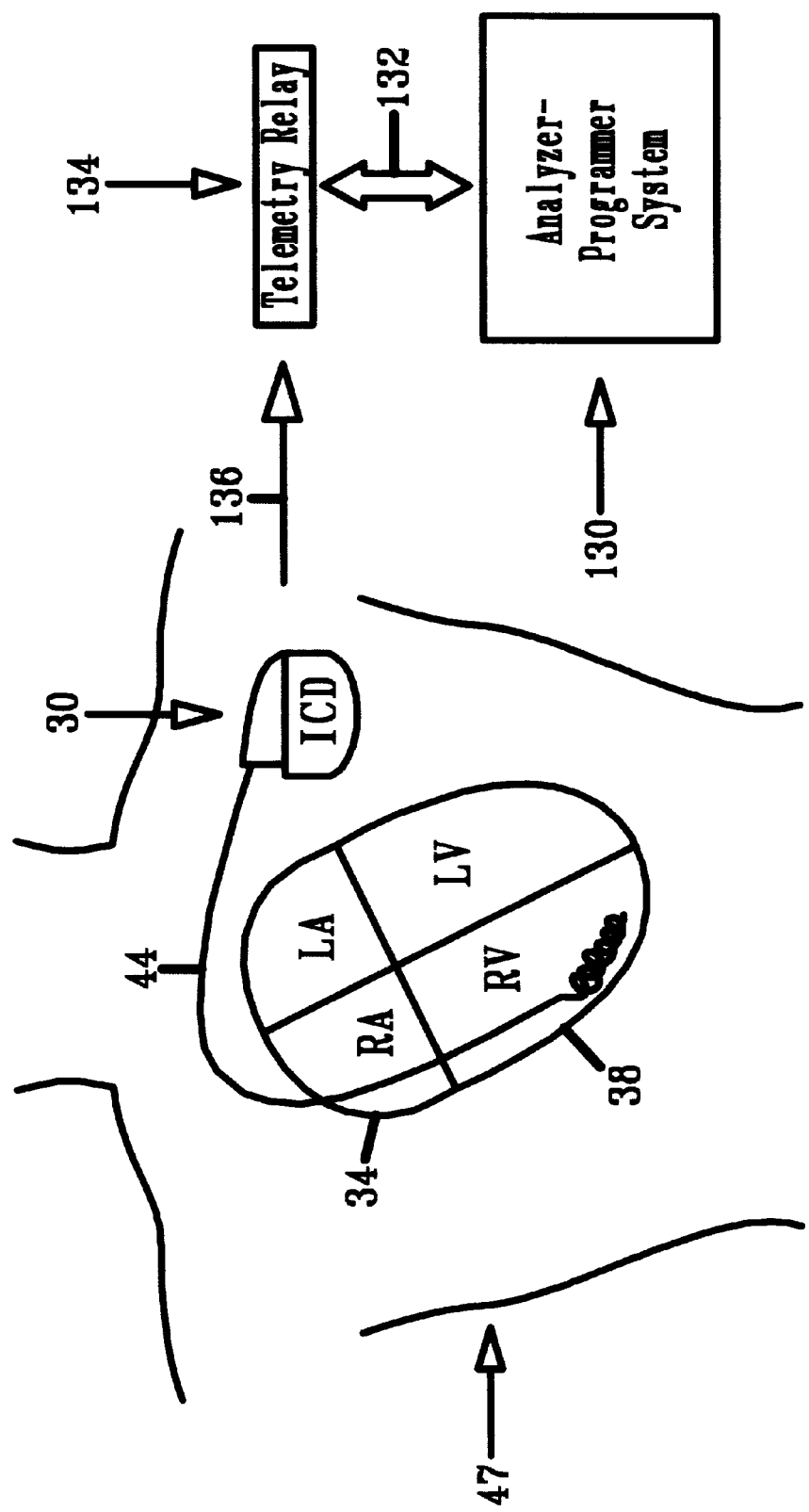
FIG. 5 illustrates the invention's primary defibrillation system components (analyzer—programmer, telemetry head, implantable cardioverter—defibrillator, and electrode system) and their interconnection for operation to implant and monitor an atrial or ventricular ICD.

The primary external components of ICD 30 are illustrated in FIG. 5. These are contrasted with the implantable elements (ICD pulse generator 30 and endocardial leads illustrated by right ventricle lead 44) which are shown within the human thorax 47 in this Figure. An analyzer-programmer system 130 is comparatively remote from the patient. Analyzer-programmer system 130 is coupled to a telemetry relay 134 via communication means 132, thereby able to compute and transmit programming instructions and programmable parameters via telemetry relay 134 to ICD 30, and able to receive programmed parameters, patient-sensed parameters, and recorded electrical activations in the form of atrial or ventricular electrograms via telemetry relay 134 from ICD 30. Telemetry relay 134 is employed near or on the patient's body to communicatively couple analyzer-programmer system 130 with ICD 30 via telemetry signals 136. The instructions and parameters are transmitted to ICD 30 and received from ICD 30 using telemetry signals 136 comprising infrared, visible, radio-frequency electromagnetic, or ultrasound radiation. Analyzer-programmer system 130 and telemetry relay 134 are well appreciated by those skilled in the art. For purposes of the present invention, these invention provisions and their general operation may correspond to inventions known in the prior art as disclosed in U.S. Pat. No. 4,809,697 issued to Causey and U.S. Pat. No. 4,958,632 issued to Duggan, both incorporated herein by reference in their entireties.

Figure 6:
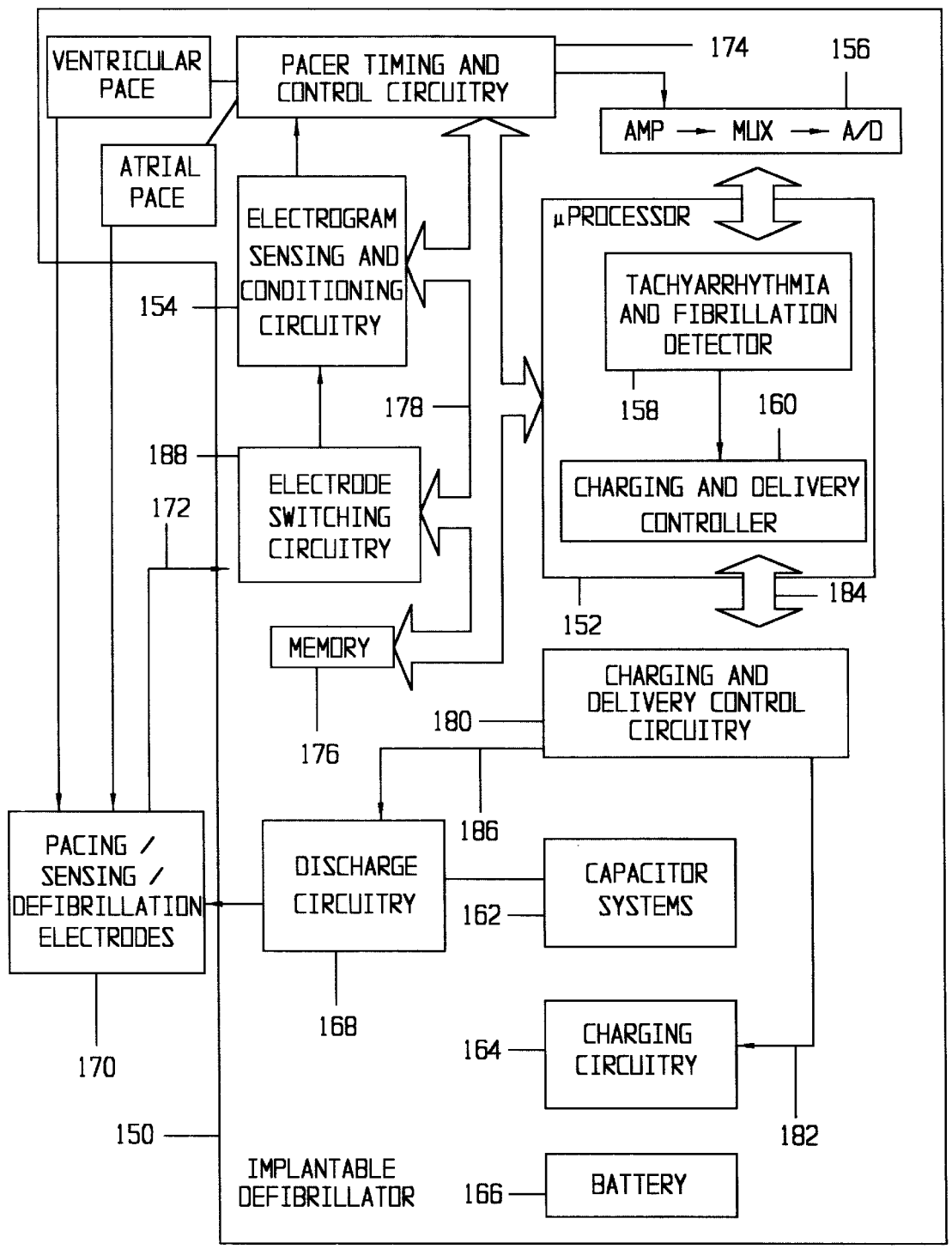
FIG. 6 illustrates the invention's primary ICD hardware and software elements and their interconnection for operation to diagnose atrial or ventricular fibrillation and to deliver reduced-pain defibrillation therapy using the principle of PPI.

The internal circuits and programming 150 of ICD 30 are illustrated in FIG. 6, and generally include electrode switching circuitry 188, electrogram sensing and conditioning circuitry 154, pacer timing/control circuitry 174, sense amplification and digitizing circuitry 156, microprocessor 152, random access memory 176, tachyarrhythmia and fibrillation detection software 158, address/data bus 178, address/data bus 184, pacing, cardioversion and defibrillation charging and delivery control software 160, charging and delivery control circuitry 180, charging circuitry 164, capacitor systems 162, discharge circuitry 168. A battery 166 is electrically and communicatively coupled to the internal circuits and programming 150 and provides a sufficient source of energy to meet all energy requirements for long-term operation of ICD 30.

Figure 8:
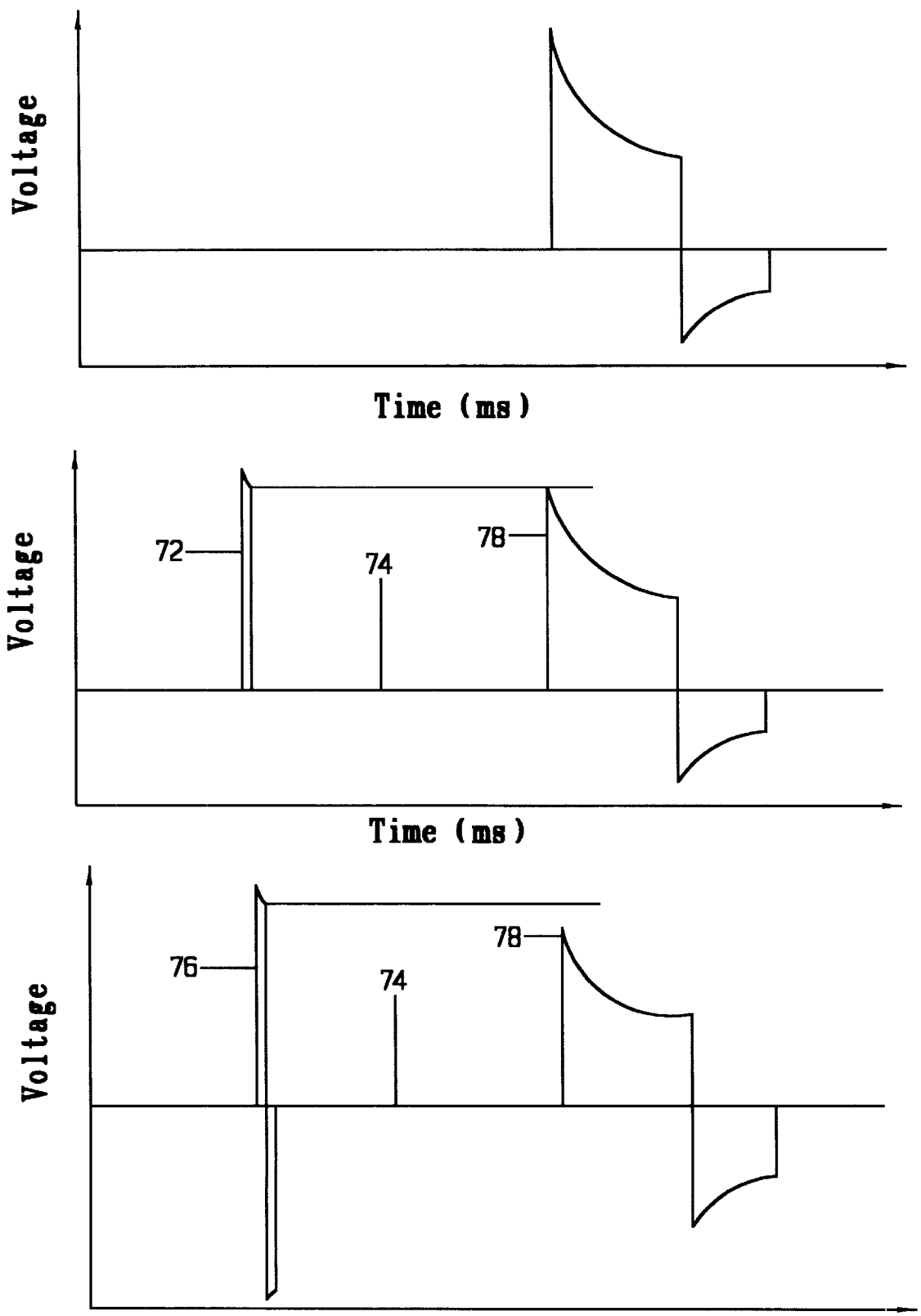
FIG. 8 illustrates first a biphasic atrial or ventricular defibrillation pulse, second a high amplitude, pain inhibiting, monophasic prepulse preceding the biphasic atrial or ventricular defibrillation pulse, and third a high amplitude, pain inhibiting, biphasic prepulse preceding the biphasic atrial or ventricular defibrillation pulse.

FIG. 7 illustrates a monophasic atrial or ventricular defibrillation pulse 70, a high amplitude, pain inhibiting, short duration, monophasic prepulse 72 preceding the monophasic atrial or ventricular defibrillation pulse, and a high amplitude, short duration, pain inhibiting, biphasic prepulse 76 preceding the monophasic atrial or ventricular defibrillation pulse. The monophasic atrial or ventricular defibrillation pulse 70 serves as the intense, painful stimulus 18 of FIG. 1. The high amplitude, short duration, pain inhibiting, monophasic prepulse 72 or the high amplitude, short duration pain inhibiting, biphasic prepulse 76 serves as the weaker prepulse 14 of FIG. 1 and is separated by a predetermined time interval 74. FIG. 8 illustrates a biphasic atrial or ventricular defibrillation pulse 78, a high amplitude, pain inhibiting, monophasic prepulse 72 preceding the biphasic atrial or ventricular defibrillation pulse, and a high amplitude, pain inhibiting, biphasic prepulse 76 preceding the biphasic atrial or ventricular defibrillation pulse. In this illustration, the biphasic atrial or ventricular defibrillation pulse 78 serves as the intense, painful stimulus 18 of FIG. 1. Note that in FIGS. 7 and 8 the weaker strength of the prepulses relative to the intense pulses is determined by pulse duration.

Figure 10:
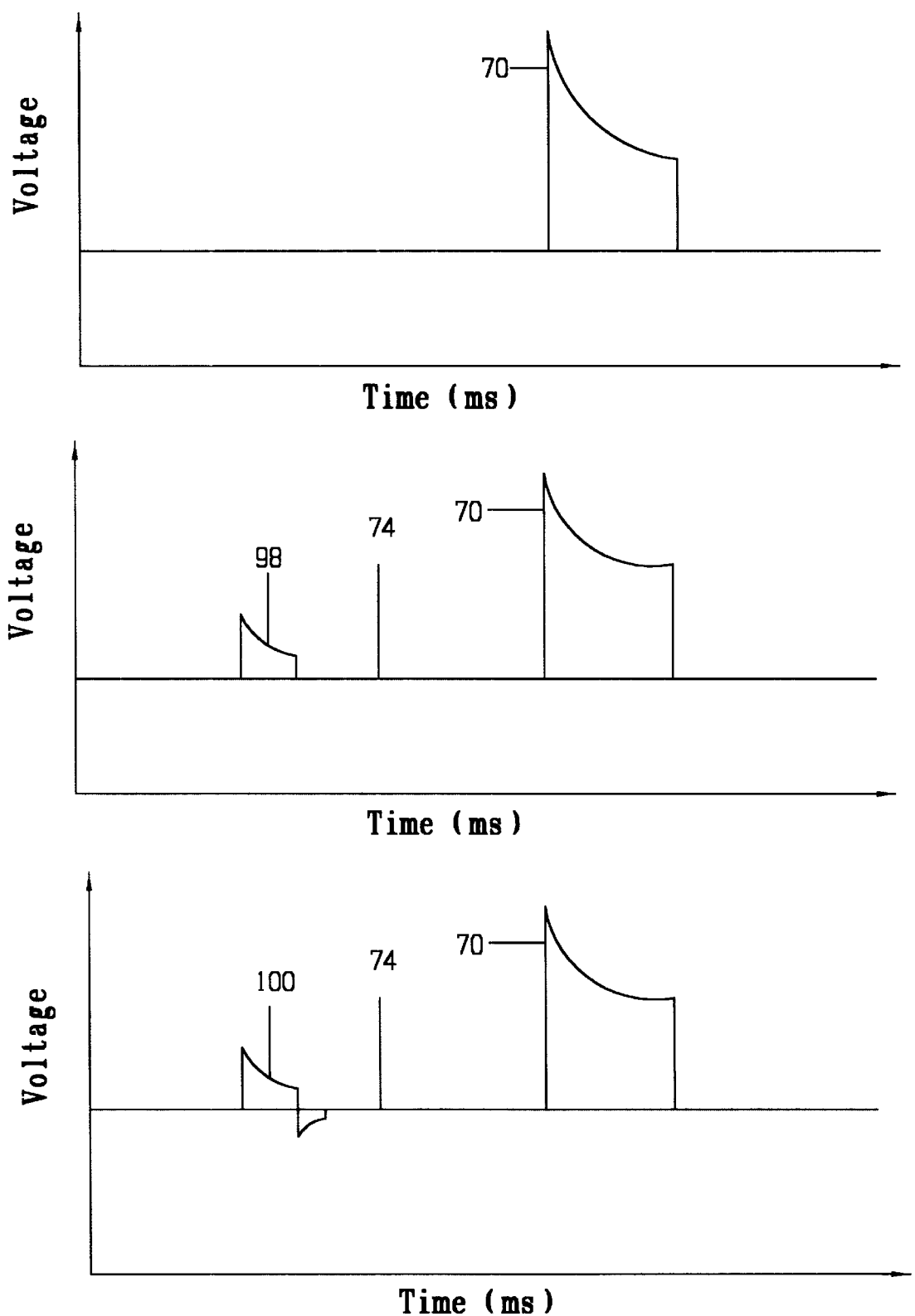
FIG. 10 illustrates first a monophasic atrial or ventricular defibrillation pulse, second a low amplitude, pain inhibiting, monophasic prepulse preceding the monophasic atrial or ventricular defibrillation pulse, and third a low amplitude, pain inhibiting, biphasic prepulse preceding the monophasic atrial or ventricular defibrillation pulse.
Figure 11:
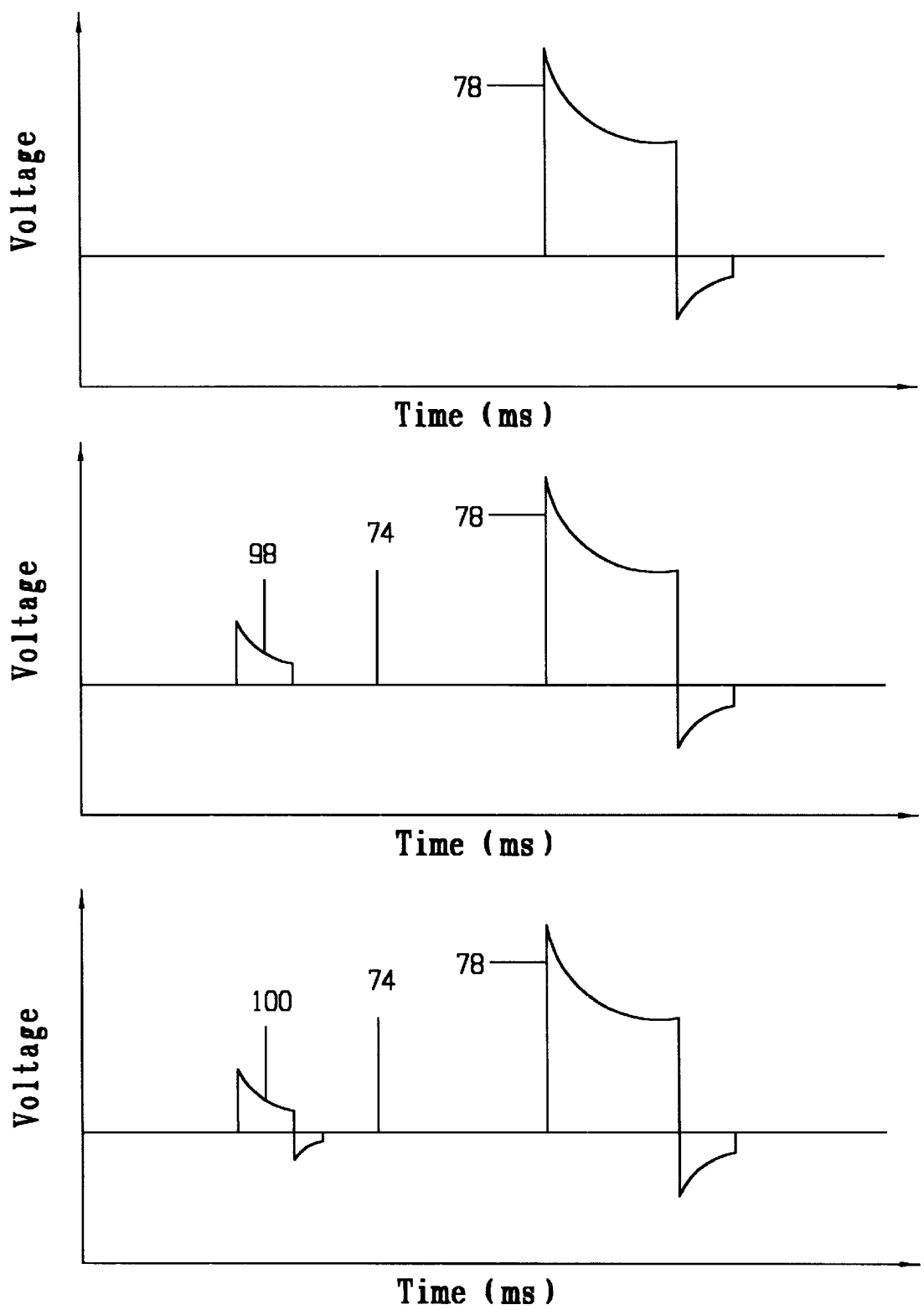
FIG. 11 illustrates first a biphasic atrial or ventricular defibrillation pulse, second a low amplitude, pain inhibiting, monophasic prepulse preceding the biphasic atrial or ventricular defibrillation pulse, and third a low amplitude, pain inhibiting, biphasic prepulse preceding the biphasic atrial or ventricular defibrillation pulse.

FIG. 10 illustrates a monophasic atrial or ventricular defibrillation pulse 70, a low amplitude, pain inhibiting, monophasic prepulse 98 preceding the monophasic atrial or ventricular defibrillation pulse, and a low amplitude, pain inhibiting, biphasic prepulse 100 preceding the monophasic atrial or ventricular defibrillation pulse. The monophasic atrial or ventricular defibrillation pulse 70 serves as the intense, painful stimulus 18 of FIG. 1, the low amplitude, pain inhibiting, monophasic prepulse 98 or the low amplitude, pain inhibiting, biphasic prepulse 100 serves as the relatively weaker prepulse 14 of FIG. 1 and is separated by a predetermined time interval 74. FIG. 11 illustrates a biphasic atrial or ventricular defibrillation pulse 78, a low amplitude, pain inhibiting, monophasic prepulse 98 preceding the biphasic atrial or ventricular defibrillation pulse, and a low amplitude, pain inhibiting, biphasic prepulse 100 preceding the biphasic atrial or ventricular defibrillation pulse. In this illustration, the biphasic atrial or ventricular defibrillation pulse 78 serves as the intense, painful stimulus 18 of FIG. 1. Note that in FIGS. 10 and 11 the weaker strength of the prepulses relative to the intense pulses is determined by pulse amplitude. This contrasts with FIGS. 7 and 8 in which the weaker strength of the prepulses relative to the intense pulses is determined by pulse duration.

Figure 9A:
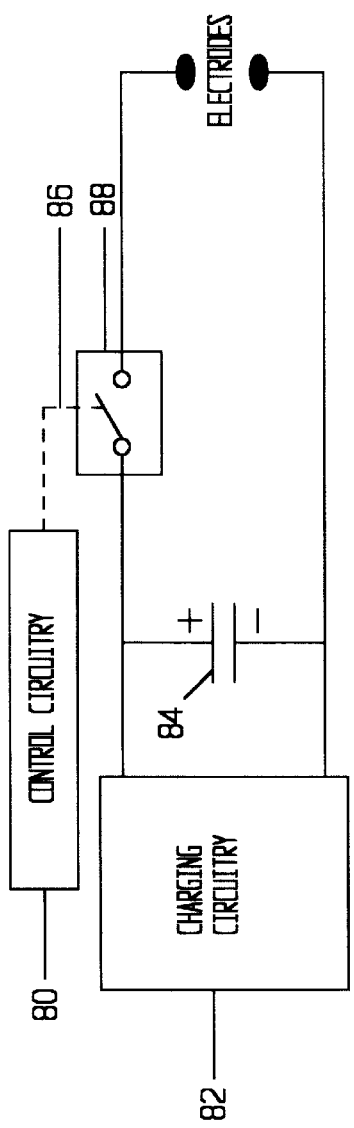
FIG. 9A illustrates control, charge, and discharge circuitry for charging and delivering a monophasic atrial or ventricular defibrillation pulse or a high amplitude, inhibiting prepulse. The circuitry illustrates charging and discharging each pulse from the same circuitry.

FIG. 9A illustrates hardware and software elements that implement the delivery of a monophasic atrial or ventricular prepulse from high-voltage defibrillation circuitry primarily designed for monophasic atrial or ventricular defibrillation waveforms. FIG. 9A illustrates charge circuitry 82, capacitor system 84, discharge control circuitry 80, monophasic discharge control lines 86, and monophasic discharge switching circuitry 88 for solid-state switching control of charging and delivering a monophasic atrial or ventricular defibrillation pulse or a high amplitude, inhibiting prepulse. Charging and delivery controller 160 of ICD 30 is coupled communicatively to the circuitry via address/data bus 184 (which may be separate from address/data bus 178). The charging portion of controller 160 operates charging circuitry 82 via control lines 182. Charge circuitry 82 charges capacitor system 84 to predetermined energy and voltage levels prior to discharge. The delivery portion of controller 160 first utilizes discharge control circuitry 80 and operates switching circuitry 88 via control lines 86 to output a monophasic, truncated exponential prepulse 72, second operates an internal timer for a predetermined amount of time to implement predetermined time interval 74, and third operates switching circuitry 88 to output a monophasic, truncated exponential cardioversion or defibrillation shock pulse 70. The circuitry illustrates charging and discharging a prepulse and a cardioversion or defibrillation pulse from the same circuitry. Prepulse 72 and 76 have leading-edge voltages equivalent to leading-edge voltages for cardioversion or defibrillation shock pulse 70. Discharge control circuitry 80 modulates the prepulse waveform duration and modulates the predetermined time interval 74.

Figure 9B:
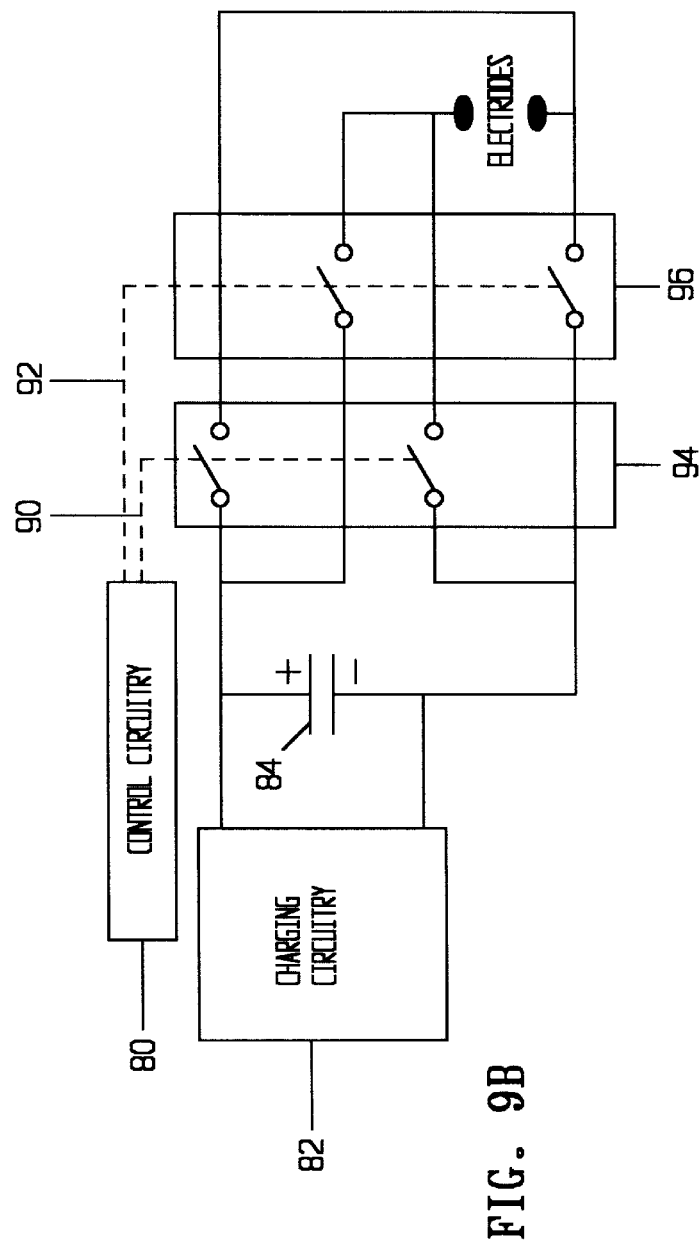
FIG. 9B illustrates control, charge, and discharge circuitry for charging and delivering a monophasic or biphasic atrial or ventricular defibrillation pulse or a high amplitude, inhibiting, monophasic or biphasic prepulse. The circuitry illustrates charging and discharging each pulse from the same circuitry.

FIG. 9B illustrates hardware and software elements that implement the delivery of a monophasic or biphasic atrial or ventricular prepulse from high-voltage defibrillation circuitry primarily designed for biphasic atrial or ventricular defibrillation waveforms. FIG. 9B illustrates charge circuitry 82, capacitor system 84, discharge control circuitry 80, monophasic or biphasic discharge control lines 90 and 92, and monophasic or biphasic discharge switching circuitry 94 and 96 for solid-state switching control of charging and delivering a monophasic or biphasic atrial or ventricular defibrillation pulse or a high amplitude, inhibiting, monophasic or biphasic prepulse. Charging and delivery controller 160 of ICD 30 is coupled communicatively to the circuitry via address/data bus 184 (which may be separate from address/data bus 178). The charging portion of controller 160 operates charging circuitry 82 via control lines 182. The charge circuitry 82 charges capacitor system 84 to predetermined energy and voltage levels prior to discharge. The delivery portion of controller 160 first utilizes discharge control circuitry 80 and operates switching circuitry 94 and 96 via control lines 90 and 92 to output a monophasic 72 or biphasic 76 truncated exponential prepulse, second operates an internal timer for a predetermined amount of time to implement predetermined time interval 74, and third operates switching circuitry 94 and 96 to output a monophasic 70 or biphasic 78 truncated exponential cardioversion or defibrillation shock pulse. FIG. 9B illustrates charging and discharging circuitry that implements biphasic waveforms using an H-bridge design. FIG. 9B further illustrates charging and discharging circuitry that output a prepulse and a cardioversion or defibrillation pulse from the same delivery circuits. Prepulse 72 and 76 have leading-edge voltages equivalent to leading-edge voltages for cardioversion or defibrillation shock pulse 70 and 78. Discharge control circuitry 80 modulates the prepulse waveform duration and modulates the predetermined time interval 74.

Capacitor system 84 illustrated in FIGS. 9A and 9B represents a conventional capacitor system for ICD 30. Capacitor system 84 is implemented with one or more electrically coupled capacitors of up to 1000 microfarads ($\mu$F) each. The electrical coupling circuitry implements effective capacitance values for ICD 30 in the range of 10 to 250 microfarads ($\mu$F), preferably in the range 60 to 120 $\mu$F. Capacitor system 84 stores 0 to 40 joules (J) of energy, preferably 2 to 20 J for ventricular defibrillation and 0.05 to 15 J for atrial defibrillation, and may be charged to 1000 V for the leading-edge voltage of prepulses 72, 76 and defibrillation shock pulses 70, 78.

Figure 12:
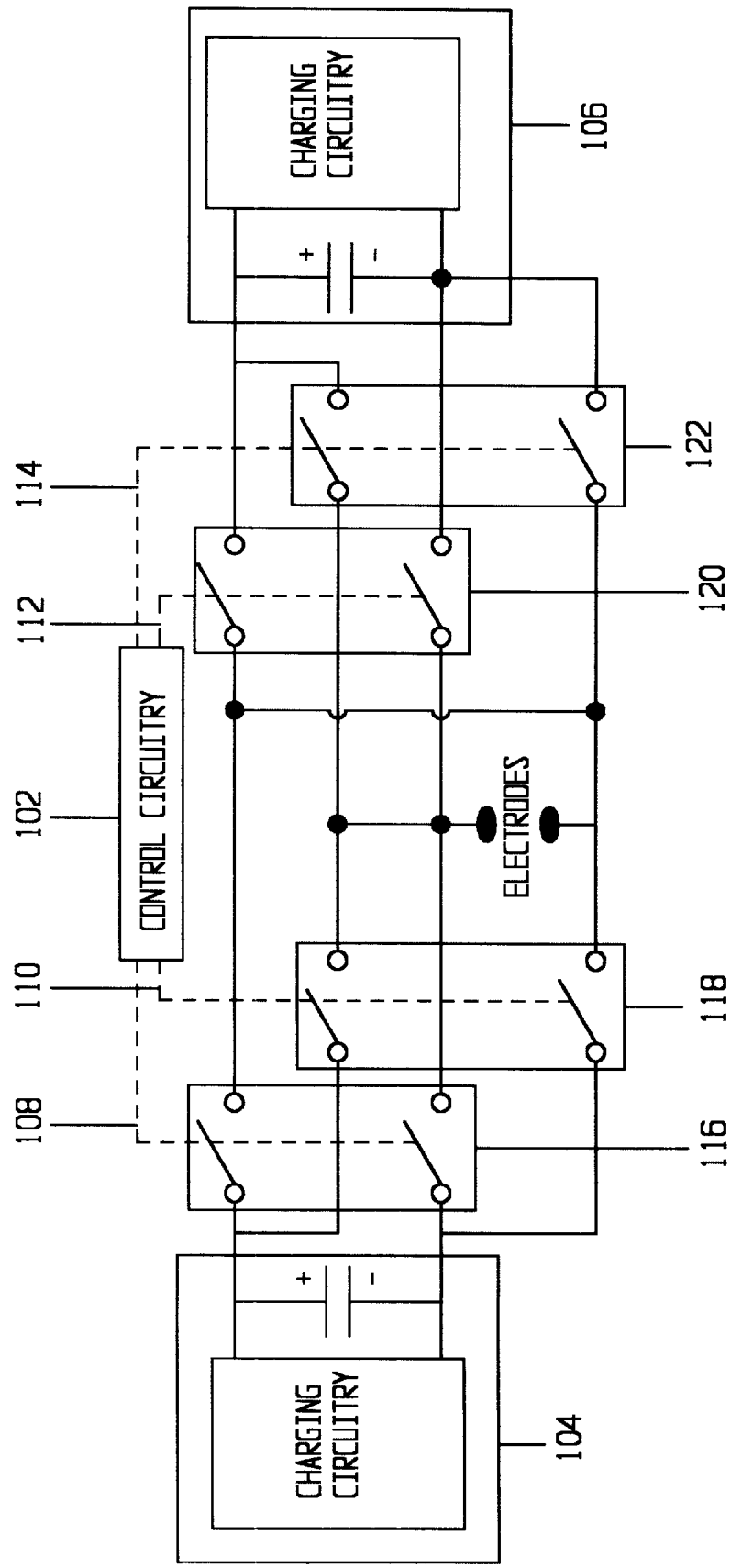
FIG. 12 illustrates control, charge, and discharge circuitry for charging and delivering a monophasic or biphasic atrial or ventricular defibrillation pulse or a low amplitude, inhibiting, monophasic or biphasic prepulse. The circuitry illustrates charging and discharging each pulse from separate circuitry.

FIG. 12 illustrates hardware and software elements that implement the delivery of a monophasic or biphasic prepulse from low-voltage, low-energy circuitry substantially different from high-voltage defibrillation circuitry that implement the delivery of high-voltage, high-energy monophasic or biphasic defibrillation waveforms. FIG. 12 illustrates charge and capacitor circuitry 104, discharge control circuitry 102, discharge control lines 108 and 110, and discharge switching circuitry 116 and 118 for a low amplitude, low-energy, monophasic or biphasic atrial or ventricular prepulse. FIG. 12 further illustrates charge and capacitor circuitry 106, discharge control circuitry 102, discharge control lines 112 and 114, and discharge switching circuitry 120 and 122 for a monophasic or biphasic atrial or ventricular defibrillation pulse. Charging and delivery controller 160 of ICD 30 is coupled communicatively to the circuitry via address/data bus 184 (which may be separate from address/data bus 178). The charging portion of controller 160 operates charging circuitry 104 and 106 via control lines 182. The charge circuitry 104 charges its capacitor system to a predetermined energy and voltage level for a low-voltage, low-energy prepulse. The charge circuitry 106 charges its capacitor system to a predetermined energy and voltage level for a high-voltage, high-energy cardioversion or defibrillation shock pulse. The delivery portion of controller 160 first utilizes discharge control circuitry 102 and operates switching circuitry 116 and 118 via control lines 108 and 110 to output a monophasic 98 or biphasic 100 truncated exponential prepulse, second operates an internal timer for a predetermined amount of time to implement predetermined time interval 74, and third utilizes discharge control circuitry 102 and operates switching circuitry 120 and 122 via control lines 112 and 114 to output a monophasic 70 or biphasic 78 truncated exponential cardioversion or defibrillation shock pulse. The circuitry illustrates charging and discharging each pulse from separate circuitry. Prepulse 98 and 100 are programmable to permit the ability to have stored energies, delivered energies, leading-edge voltages, and prepulse waveform shapes substantially different from the stored energies, delivered energies, and leading-edge voltages for cardioversion or defibrillation shock pulse 70 and 78. Discharge control circuitry 102 modulates the prepulse waveform phase durations and amplitudes, and modulates the predetermined time interval 74.

Capacitor systems 104 and 106 illustrated in FIG. 12 represent conventional capacitor systems for ICD 30. Capacitor systems 104 and 106 may each be implemented with one or more electrically coupled capacitors of up to 1000 microfarads ($\mu$F) each. Electrical coupling circuitry for each capacitor system implements effective capacitance values for ICD 30 in the range of 10 to 250 microfarads ($\mu$F), preferably in the range 60 to 120 $\mu$F. Capacitor systems 104 and 106 each store 0 to 40 joules (J) of energy, preferably 2 to 20 J for ventricular defibrillation and 0.05 to 15 J for atrial defibrillation, and each system may be charged to 1000 V for the leading-edge voltage of prepulses 98, 100 and defibrillation shock pulses 70, 78. Independent capacitor systems 104 and 106 provide for prepulse waveform design substantially similar or substantially different from cardioversion and defibrillation waveform designs, as illustrated in FIGS. 7, 8, 10 and 11. In a preferred embodiment, capacitor system 104 is designed with different capacitive values and energy capabilities from the capacitance and energy capabilities of capacitor system 106. Capacitor system 104 implements the prepulse therapy with different capacitor values, stored and delivered energies, leading-edge voltages, and waveform shapes. Alternatively, capacitor system 104 implements a square waveform and rounded waveform as a prepulse. Capacitor systems 104 may be implemented as a pacing circuit and provide pacing pulses for prepulses 98 and 100.

The remainder of the invention is dedicated to the provision of cardiac pacing, cardioversion, defibrillation therapies, and apparatus programming techniques. For purposes of the present invention, these invention provisions may correspond to inventions known in the prior art. An exemplary apparatus is disclosed of accomplishing pacing, cardioversion, defibrillation, and programming functions. The general operation of the apparatus may correspond to that apparatus disclosed in U.S. Pat. No. 5,549,642 issued to Min, incorporated herein by reference in its entirety. As cited earlier, the exemplary apparatus is illustrated by FIGS. 4A through 12.

As illustrated in FIG. 4A, sensing electrodes 52 are located on or in the right ventricle 38 and are coupled to the R-wave detection section of the electrogram sensing and conditioning circuitry 154, which preferably takes the form of an automatic threshold controlled sensing circuit providing an adjustable sensing threshold as a function of the measured electrogram amplitude. As illustrated in FIG. 4B, sensing electrodes 50 are located on or in the right atrium 34 and are coupled to the P-wave detection section of the electrogram sensing and conditioning circuitry 154, which preferably takes the form of an automatic threshold controlled sensing circuit providing an adjustable sensing threshold as a function of the measured electrogramn amplitude. The general operation of the P-wave and R-wave sensing and conditioning circuitry 154 may correspond to circuitry disclosed in U.S. Pat. No. 5,117,824 issued to Keimel and U.S. Pat. No. 5,282,837 issued to Adams, incorporated herein by reference in their entireties. Electrode switching circuitry 188 is used to select which of the available electrodes are coupled to the electrogram sensing and conditioning circuitry 154 for use in digital signal analysis. Selection of electrodes is controlled by microprocessor 152 using the data and address bus 178, which selections may be varied as desired. Signals from the selected electrodes are provided to the wide band (0.02–200 Hz) amplifier, multiplexer, and analog to digital converter circuitry 156 for conversion to multi-bit digital signals and to the random access memory 176 under the control of the microprocessor 152 for storage. Microprocessor 152 may employ digital signal processing techniques to characterize the digitized signals stored in memory 176 to recognize and classify the patient's heart rhythm. Microprocessor 152 may employ any of the numerous signal processing methods known to the art.

The pacer timing/control circuitry 174 includes programmable digital counters which control the basic time intervals associated with DDD, VVI, DVI, VDD, AAI, DDI, and other modes of single and dual chamber pacing well known to the art. Circuitry also controls escape intervals associated with antitachyarrhythmia pacing in both the atrium and the ventricle, employing any antitachyarrhythmia pacing therapies known to the art.

Intervals defined by pacing circuitry 174 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 152, in response to stored data in memory 176 and are communicated to the pacing circuitry 174 via address/data bus 178. Pacer circuitry 174 also determines the amplitude of the cardiac pacing pulses under the control of the microprocessor 152.

During pacing, the escape interval counters within pacer timing/control circuitry 174 are reset upon sensing of R-waves and P-waves as indicated by signals on address/data bus 178, in accordance with the selected mode of pacing on time-out trigger generation of pacing pulses by pacer output circuitry, which are coupled to electrodes 50 and 52. The escape interval counters are also reset on generation of pacing pulses, and thereby control the basic timing of cardiac pacing functions, including tachyarrhythmia pacing. The durations of the intervals defined by the escape interval timers are determined by microprocessor 152, via address/data bus 178. The value of the count present in the escape interval counters when reset by sensed R-waves and P-waves may be used to measure the durations of R—R intervals, P—P intervals, P-R intervals, and R-P intervals, which measurements are stored in memory 176 and used to detect the presence of tachyarrhythmias.

Microprocessor 152 operates as an interrupt driven device, and is responsive to interrupts from pacer timing/control circuitry 174 corresponding to the occurrence sensed P-waves and R-waves and corresponding to the generation of cardiac pacing pulses. These interrupts are provided via address/data bus 178. Any necessary mathematical calculations to be performed by microprocessor 152 and any updating of the values or intervals controlled by pacer timing/control circuitry 174 take place following such interrupts.

For example, in response to a sensed or paced ventricular depolarization or R-wave, the intervals separating that R-wave from the immediately preceding R-wave, paced or sensed (R—R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P—P interval) and the interval separating the sensed P-wave from the immediately preceding sensed or paced ventricular depolarization (R-P interval) may be stored. Preferably, a portion of the memory 176 is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

The tachyarrhythmia and fibrillation detector 158 operates the algorithms that process the arrhythmia signal data stored in memory 176. Detection of atrial or ventricular tachyarrhythmias, as employed in the present invention, may correspond to tachyarrhythmia detection algorithms known to the art. There are many algorithms known in the art for processing arrhythmia data to determine if an atrial or ventricular tachyarrhythmia is present. For example, presence of atrial or ventricular tachyarrhythmia may be confirmed by means of detection of a sustained series of short R—R or P—P intervals. The average cycle length, median cycle length, or cycle length of a certain percentage of intervals (e.g. 75% or 100%) is less than the corresponding, programmed tachyarrhythmia detection interval and thus indicative of a tachyarrhythmia. The suddenness of onset of the detected high rates in each chamber, the interval stability of the high rate P—P and R—R intervals the presence or absence of P-R association, information related to the morphology of the electrograms corresponding to P and R waves in each chamber, or a number of other factors known to the art may also be measured at this time. Appropriate ventricular tachyarrhythmia detection methodologies measuring such factors are described in U.S. Pat. No. 4,726,380 issued to Vollmann, U.S. Pat. No. 4,830,006 issued to Haluska, U.S. Pat. No. 4,880,005 issued to Pless, U.S. Pat. No. 5,251,626 issued to Nickolls, and U.S. Pat. No. 5,545,186 issued to Olson, all incorporated herein by reference in their entireties. An additional set of tachycardia recognition methodologies is disclosed by Olson (Onset and stability for ventricular tachyarrhythmia detection in an implantable pacer-cardioverter-defibrillator, Computers in Cardiology, Oct. 7–10, 1986, IEEE Computer Society Press, pages 167–170) also incorporated herein in its entirety. However, the advantages of the present invention is clearly practicable in conjunction with most prior art tachycardia detection algorithms. Atrial fibrillation detection methodologies in particular are disclosed in U.S. Pat. No. 5,205,283 issued to Olson and U.S. Pat. No. 5,282,837 issued to Adams, in the publication by Arzbaecher (Arzbaecher et al, Automatic tachycardia recognition, PACE 1984; 541–547), and in the publication by Thakor (Thakor et al, Ventricular tachycardia and fibrillation detection by a sequential hypothesis testing algorithm, IEEE Trans Biomedical Engineering 1990; 37: 837–843), all of which are incorporated herein by reference in their entireties. Implementing such atrial and ventricular arrhythmia detection algorithms by a microprocessor is well within the preview of one skilled in the art.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 152 into the pacing timing and control circuitry 174 to control the operation of the escape interval counters therein and to define refractory periods during which detection of P-waves and R-waves is ineffective to restart the escape intervals.

Alternatively, circuitry for controlling the timing and generation of antitachycardia pacing pulses as described in U.S. Pat. No. 4,577,633 issued to Berkovits, U.S. Pat. No. 4,587,970 issued to Holley, U.S. Pat. No. 4,726,380 issued to Vollman, and U.S. Pat. No. 4,880,005 issued to Pless, all of which are incorporated herein by reference in their entireties, may also be used.

In the event that generation of a cardioversion or defibrillation pulse is required, microprocessor 152 employs an escape interval counter to control timing of such cardioversion and defibrillation pulses, as well as associated refractory periods. In response to the detection of atrial or ventricular fibrillation or tachyarrhythmia requiring a cardioversion pulse, microprocessor 152 activates the therapy charging and delivery controller 160 and the therapy charging and delivery control circuitry 180, which initiates charging of the high voltage capacitor systems 162 via the charging circuit 164 powered by the battery 166 and under the control of high voltage charging control lines 182. The voltage on the high voltage capacitors is monitored, and in response to reaching a predetermined value set by microprocessor 152, results in generation of a logic signal that terminates the charging of the capacitor systems 162. Thereafter, timing of the delivery of the defibrillation or cardioversion pulse is controlled by the therapy charging and delivery controller 160 and the therapy charging and delivery control circuitry 180. Following delivery of the fibrillation or tachycardia therapy the microprocessor 152 then returns the device to cardiac pacing and awaits the next successive interrupt due to pacing or the occurrence of a sensed atrial or ventricular depolarization. As described in preceding paragraphs, the control, charging, and delivery circuitry and logic for the pain-suppressing prepulse therapies of the present invention are embodied within the structural framework of the modern implantable cardioverter—defibrillator as described herein.

One embodiment of an appropriate system for delivery and synchronization of ventricular cardioversion and defibrillation pulses and for controlling the timing functions related to them is disclosed in more detail in U.S. Pat. No. 5,188,105 issued to Keimel, incorporated herein by reference in its entirety. Embodiments of appropriate systems for delivery and synchronization of atrial cardioversion and defibrillation pulses and for controlling the timing functions related to them are disclosed in more detail in U.S. Pat. No. 4,316,472 issued to Mirowski and in U.S. Pat. No. 5,269,298 issued to Adams, both incorporated herein by reference in their entireties. However, any known cardioversion or defibrillation pulse control circuitry is believed usable in conjunction with the present invention. For example, circuitry controlling the timing and generation of cardioversion and defibrillation pulses as disclosed in U.S. Pat. No. 4,375,817 issued to Engle, in U.S. Pat. No. 4,384,585 issued to Zipes, and in U.S. Pat. No. 4,949,719 issued to Pless, all incorporated herein by reference in their entireties, may also be employed.

In the illustrated apparatus, delivery of the cardioversion or defibrillation pulses is accomplished by the therapy discharge circuitry 168, under control of circuitry 180 via control bus 186. Therapy control circuitry 180 determines whether a monophasic or biphasic pulse is delivered, the polarity of the electrodes, and which electrodes are involved in delivery of the pulse. Therapy discharge circuitry 168 includes high voltage switches which control which electrodes 40, 42, 44, and 46 are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in U.S. Pat. No. 4,727,877 issued to Kallok and in U.S. Pat. No. 4,953,551 issued to Mehra, both incorporated herein by reference in their entireties. An example of circuitry which may be used to control delivery of monophasic pulses is set forth in U.S. Pat. No. 5,163,427 issued to Keimel, incorporated herein by reference in its entirety. However, output control circuitry as disclosed in the previously cited U.S. Pat. No. 4,953,551 issued to Mehra, or U.S. Pat. No. 4,800,883 issued to Winstrom, incorporated herein by reference in its entirety, may also be used in conjunction with a apparatus embodying the present invention for delivery of biphasic pulses.

In the event that both atrial and ventricular defibrillation are available, ventricular defibrillation may be accomplished using higher pulse energy levels than required for atrial defibrillation and may employ the same or a different electrode set as those electrodes used for atrial defibrillation. For example, electrodes 40 (right atrial/superior vena cava) and 42 (coronary sinus/great vein) may be employed for atrial defibrillation. Electrodes 40 and 44 (right ventricle) might be employed for ventricular defibrillation, with electrode 40 coupled to electrode 46 (device housing). One particularly desirable embodiment of the invention employs only the right atrial/superior vena cava electrode 40, the coronary sinus/great cardiac vein electrode 42 and the right ventricular electrode 44. During atrial defibrillation, electrodes 40 and 46 are coupled in common to one another, and the atrial defibrillation pulse is delivered between these electrodes and electrodes 42. During ventricular defibrillation, electrodes 40 and 46 are coupled in common with one another, and the ventricular defibrillation pulse is delivered between these electrodes and electrode 44. This particular set of electrodes thus provides optimized defibrillation pulse regimens for both atrial and ventricular defibrillation, by simply switching the software or hardware controlled connections of the coronary sinus/great vein electrode 42 and the right ventricle electrode 44. In another particularly desirable embodiment of the invention the same lead configuration is used for both atrial and ventricular defibrillation. Electrodes 40 and 46 are coupled in common with one another, and the atrial or ventricular defibrillation pulse is delivered between these electrodes and electrode 44. This particular set of electrodes avoids the need for a coronary sinus/great vein electrode 42 and facilitates delivery of an atrial defibrillation shock with a strength that exceeds the ventricular upper limit of vulnerability.

Functional switching circuitry well known in the art may be employed in high voltage output circuit 168, such that the circuitry includes high voltage switches individually controlled by signals on control bus 186. These switches allow connection of any of the described electrodes to either the positive or the negative terminals of the capacitor systems 162. As illustrated, any combination of electrodes may be selected, any polarities desired may be provided, and monophasic or biphasic pulses may be delivered, depending upon control signals on control bus 184. In the event that a reduced set of available electrode configurations is desired, the switching circuitry may be simplified. An example of switching circuitry may be found in the cited patent issued to Min (U.S. Pat. No. 5,549,642).

In modern ICDs, the particular therapies are programmed into the device at the time of implant or later by the physician, and a menu of therapies is typically provided for such programming by the analyzer-programmer system 130. For example, on initial detection of an atrial or ventricular tachycardia, an antitachycardia pacing therapy may be selected and delivered to the chamber in which the tachycardia is diagnosed or to both chambers. On redetection of tachycardia, a more aggressive anti-tachycardia pacing therapy may be delivered. If repeated attempts at anti-tachycardia pacing therapies fail, a higher voltage cardioversion pulse may be selected thereafter. Therapies for tachycardia termination may also vary with the rate of the detected tachycardia, with the therapies increasing in aggressiveness as the rate of the detected tachycardia increases. For example, fewer attempts at anti-tachycardia pacing may be undertaken prior to delivery of cardioversion pulses if the rate of the detected tachycardia is above a preset threshold. The cited references in conjunction with descriptions of prior art tachycardia detection and treatment therapies are applicable here as well. As described in preceding paragraphs, the programming logic and algorithms for the pain-suppressing prepulse therapies of the present invention are embodied within the structural framework for programming modern ICDs as described herein.

In the event that atrial or ventricular fibrillation is identified, the typical therapy will be delivery of a high amplitude defibrillation pulse, typically 10 joules or more in the case of ventricular fibrillation and 10 joules or less in the case of atrial defibrillation. Lower energy levels will be employed for cardioversion. As in the case of currently available implantable pacemakers and ICDs, and as discussed in the cited references, it is envisioned that the amplitude of the defibrillation pulse may be incremented in response to failure of an initial pulse to terminate fibrillation. Prior art patents illustrating such pre-set therapy menus of anti-tachycardia therapies include the previously cited U.S. Pat. No. 4,587,970 issued to Holley, U.S. Pat. No. 4,726,380 issued to Vollmann, and U.S. Pat. No. 4,830,006 issued to Haluska.

While the invention that is disclosed is embodied in a dual chamber pacemaker and ICD, the invention may also be usefully practiced in substantially simpler devices. For example, the illustrated defibrillation electrodes may simply be coupled to an implantable atrial cardioverter as disclosed in U.S. Pat. No. 3,738,370 issued to Charms and U.S. Pat. No. 5,282,837 issued to Adams, incorporated herein by reference in their entireties. Similarly, while the electrodes employed for atria sensing and pacing are disclosed as mounted to the atrial lead, these electrodes might alternatively take the form of ring electrodes mounted to either the ventricular lead or the coronary sinus/great vein lead or on a separate electrode.

From the foregoing preferred embodiments, it can be seen that the present invention provides a new and improved fully implantable atrial defibrillator and a new and improved fully implantable cardioverter—defibrillator, each of which is fully automatic and which is safe in use.

Description of the Principle Methods

ICD pulse generator 30 is implanted in a pectoral or abdominal pocket. When an arrhythmia occurs, ICD 30 detects it and charges the output capacitors. ICD 30 also activates the circuits required to deliver the prepulse. After the output capacitors for the therapeutic pulse are charged, ICD 30 may optionally confirm that the arrhythmia persists. In atrial fibrillation, ICD 30 may also wait until the interval between sensed QRS complexes exceeds a predetermined, programmable value to minimize the risk of inducing ventricular fibrillation by a shock in the ventricle's vulnerable period. A typical minimum interval is 500 ms.

The prepulse is delivered synchronously with the sensed QRS complex. The prepulse is synchronized to the local bipolar electrogram recorded from the right-ventricular sensing electrodes 52 or to a far-field electrogram which uses the active housing 46 or right-ventricular defibrillating electrode 44. ICD 30 may transmit a telemetry pulse at the time of prepulse delivery. This telemetry pulse can be detected by analyzer-programmer system 130 and telemetry relay 134 for ICD 30. The therapeutic shock is delivered 20–200 ms later. The preferred interval between the prepulse and therapeutic pulse is the shortest interval which optimizes PPI. Optimal PPI occurs at time intervals of approximately 100 ms, well within the ventricle's absolute refractory period. A shortest, optimal prepulse interval eliminates the risk of inducing ventricular fibrillation by a therapeutic shock delivered during atrial fibrillation or ventricular tachycardia. The strength of therapeutic shocks can be less than a ventricle's upper limit of vulnerability, and therefore the therapeutic shock is delivered with a sufficiently short interval after the sensed QRS complex to precede the inner limit of vulnerability at the therapeutic shock strength. Therefore, the prepulse is synchronized at QRS complex onset (Hou et al, Determination of ventricular vulnerable period and ventricular fibrillation threshold by use of T-wave shocks in patients undergoing implantation of cardioverter—defibrillators, Circulation 1995; 92: 2558–2564). In patients with right-ventricular conduction delays, synchronization to a far-field electrogram may be required because the bipolar right-ventricular electrogram occurs late in the QRS complex.

The prepulse may be an electrical, auditory, or vibro-tactile stimulus. ICD 30 may deliver the prepulse over the same electrode system used to deliver the therapeutic shock or over a different pathway. Prepulses may include the following: (1) electrical pulses delivered between two cardiac (endocardial, epicardial, or extrapericardial) electrodes or between one intracardiac electrode and an extracardiac electrode, for example right atrial/superior vena cava electrode 40, housing electrode 46, or a subcutaneous electrode (not illustrated); (2) electrical pulses delivered between two extra cardiac electrodes including any combination of the housing 46, small electrodes suspended from and electrically coupled to ICD 30, an additional electrode in the ICD pocket or an adjacent pocket, or an electrode implanted at a distance from the pocket; (3) acoustic pulses delivered from a speaker in ICD 30; or (4) vibro-tactile stimuli delivered to muscle, bone, or nerve via ICD 30 or from a remote stimulator controlled by the pulse generator. In the last case, communication between the pulse generator and ICD 30 may be described by standard wire or wireless methods in a same manner as telemetry communications.

If an electrical prepulse is used, the range of prepulse stimulus strengths vary from 5 V to 1000 V and the duration of prepulse stimuli from 0.1 ms to 25 ms. The preferred strengths are in the range of 10 V to 100 V with preferred durations from 1 ms to 10 ms. Auditory stimuli vary in intensity from 0.1 dB(A) to 100 dB(A) above ambient noise and from 0.1 ms to 100 ms in duration. The preferred strengths range from 5 dB(A) to 15 dB(A) above ambient noise with durations from 15 ms to 25 ms.

Optimal prepulse characteristics are determined on a patient-specific basis or are preset with default parameters. The method for programming a patient specific prepulse intensity and interval is as follows: The initial prepulse interval is set near the median optimal interval for the population (about 100 ms), and the initial intensity is set slightly below the median sensory threshold. The prepulse is then delivered synchronously with a QRS complex. If it is below the patient's sensory threshold, the stimulus strength is incremented, and the process is iterated until the patient identifies the prepulse reliably. The prepulse intensity is further increased in small increments until the patient judges the prepulse to be slightly uncomfortable. It is then programmed to a level slightly below this discomfort level.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. An apparatus for cardioverting or defibrillating a patient's heart, comprising:
a set of cardioversion electrodes applicable to the patient's body;
means for applying a patient-perceptible stimulus to a portion of the patient's body other than the patient's heart other than by means of the set of cardioversion electrodes; and
means for delivering a high voltage shock to the patient's heart by means of electrodes within the set of cardioversion electrodes within 20 to 500 milliseconds following initiation of the patient perceptible stimulus.

2. The apparatus of claim 1 wherein the means for applying the patient-perceptible stimulus comprises means for applying electrical stimulation.

3. The apparatus of claim 2 wherein the means for applying electrical stimulation comprises means for applying electrical stimulation of at least 10 volts.

4. The apparatus of claim 3 wherein the means for applying electrical stimulation comprises means for applying electrical stimulation of less than 1000 volts.

5. The apparatus of claim 3 wherein the means for applying electrical stimulation comprises the means for applying electrical stimulation of less than 100 volts.

6. The apparatus of claim 3 wherein the means for applying electrical stimulation comprises means for applying electrical stimulation for a period of 0.05 to 25 milliseconds.

7. The apparatus of claim 1 wherein the means for applying the patient-perceptible stimulus comprises means for delivering auditory stimulation.

8. The apparatus of claim 7, wherein the means for delivering auditory stimulation comprises means for delivering auditory stimulation at an intensity from 0.1 dB(A) to 100 dB(A) above an existing ambient noise level.

9. The apparatus of claim 8, wherein the means for delivering auditory stimulation comprises means for delivering auditory stimulation at an intensity from 5 dB(A) to 15 dB(A) above said existing ambient noise level.

10. The apparatus of claim 1 wherein the means for applying the patient-perceptible stimulus comprises means for delivering tactile stimulation.

11. The apparatus of claim 1 wherein the means for applying the patient-perceptible stimulus comprises means for applying stimulation to a body part selected from the group of the patient's body parts comprising the patient's ear, skeletal muscle, bone, or nerve.

12. An apparatus for delivering a painful treatment to a portion of a patient's body comprising:

applying means for delivery of the painful therapy to a first portion of the patient's body;

means for applying a patient-perceptible stimulus to a second, portion of the patient's body other than the first portion employing means other than the means for delivery of the painful therapy; and means for delivering the painful therapy within 20 to 500 milliseconds following initiation of the patient-perceptible stimulus.

13. The apparatus of claim 12 wherein the means for applying a patient-perceptible stimulus comprises means for applying electrical stimulation.

14. The apparatus of claim 13 wherein the means for applying electrical stimulation comprises means for applying electrical stimulation of at least 10 volts.

15. The apparatus of claim 13 wherein the means for applying electrical stimulation comprises means for applying electrical stimulation of less than 1000 volts.

16. The apparatus of claim 15 wherein the means for applying electrical stimulation comprises means for applying electrical stimulation of less than 100 volts.

17. The apparatus of claim 13 wherein the means for applying electrical stimulation comprises means for applying electrical stimulation for a period of 0.05 to 25 milliseconds.

18. The apparatus of claim 12 wherein the means for applying a patient-perceptible stimulus comprises means for delivering auditory stimulation.

19. The apparatus of claim 18, wherein the means for delivering auditory stimulation comprises means for delivering auditory stimulation at an intensity from 0.1 dB(A) to 100 dB(A) above an existing ambient noise level.

20. The apparatus of claim 19, wherein the means for delivering auditory stimulation comprises means for delivering auditory stimulation at an intensity from 5 dB(A) to 15 dB(A) above said existing ambient noise level.

21. The apparatus of claim 12 wherein the means for applying a patient-perceptible stimulus comprises means for applying tactile stimulation.

22. The apparatus of claim 12 wherein the means for applying a patient-perceptible stimulus comprises means for applying stimulation to a body part selected from the group of the patient's body parts comprising the patient's ear, skeletal muscle, bone, or nerve.

23. The apparatus of claim 1 or claim 12 wherein the means for delivering the painful therapy comprises means for delivering a cardioversion or defibrillation pulse.

* * * * *